US010463701B2

(12) United States Patent
Remus et al.

(10) Patent No.: US 10,463,701 B2
(45) Date of Patent: *Nov. 5, 2019

(54) **BLENDS OF *BACILLUS* STRAINS AND ENZYMES**

(71) Applicant: DUPONT NUTRITION BIOSCIENCES APS, Copenhagen (DK)

(72) Inventors: Janet Remus, Spicer, MN (US); Randolph Chick, Fayetteville, AR (US); Nuntawadee Sriperm, Buford, GA (US); Tammy Baltzley, Horicon, WI (US); Milan Hruby, Woodbury, MN (US)

(73) Assignee: DUPONT NUTRITION BIOSCIENCE APS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,113

(22) Filed: Dec. 30, 2014

(65) Prior Publication Data

US 2015/0290254 A1    Oct. 15, 2015

Related U.S. Application Data

(60) Provisional application No. 61/922,257, filed on Dec. 31, 2013.

(51) Int. Cl.
| | | |
|---|---|---|
| *A61K 35/74* | (2015.01) | |
| *A61K 38/47* | (2006.01) | |
| *A61K 38/48* | (2006.01) | |
| *A61K 35/00* | (2006.01) | |

(52) U.S. Cl.
CPC .............. *A61K 35/74* (2013.01); *A61K 38/47* (2013.01); *A61K 38/482* (2013.01); *C12Y 302/01008* (2013.01); *A61K 2035/11* (2013.01)

(58) Field of Classification Search
CPC .... A23K 1/1653; A23K 1/009; A23K 1/1603; A23K 1/175; A23K 1/184; C12Y 301/03008; C12Y 301/03026
See application file for complete search history.

(56) References Cited

U.S. PATENT DOCUMENTS

| | | | |
|---|---|---|---|
| 5,902,581 A | 5/1999 | Clarkson et al. | |
| 6,287,841 B1 | 9/2001 | Mulleners et al. | |
| 9,179,693 B2 * | 11/2015 | Romero | A23K 1/1653 |
| 2014/0234279 A1 * | 8/2014 | Millan | A23K 1/009 |
| | | | 424/93.41 |

FOREIGN PATENT DOCUMENTS

| | | |
|---|---|---|
| EP | 0120693 | 10/1984 |
| GB | 1011513.7 | 8/2010 |
| WO | WO1989006270 | 7/1989 |
| WO | WO1989006279 | 7/1989 |
| WO | WO1991004669 | 4/1991 |
| WO | WO1992012645 | 8/1992 |
| WO | WO1992019729 | 11/1992 |
| WO | WO1994025583 | 11/1994 |
| WO | WO1997016076 | 5/1997 |
| WO | WO1998020115 | 5/1998 |
| WO | WO2007044968 | 4/2007 |
| WO | WO2012004759 | 1/2012 |
| WO | WO 2012/110778 * | 8/2015 |

OTHER PUBLICATIONS

U.S. Appl. No. 13/985,863 and U.S. Appl. No. 14/512,925.*
Bailey, et al., (May 1992) Journal of Biotechnology, vol. 23, (3), pp. 257-270.

* cited by examiner

*Primary Examiner* — Ruth A Davis

(57) ABSTRACT

Compositions and methods are disclosed for providing beneficial effects to animals, including but not limited to increasing performance of the animal. In one embodiment, the animal is poultry. In another embodiment, the disclosure relates to a composition comprising one or more direct-fed microbials and one or more exogenous feed enzymes.

21 Claims, No Drawings

Specification includes a Sequence Listing.

BLENDS OF *BACILLUS* STRAINS AND ENZYMES

CROSS-REFERENCE TO RELATED APPLICATIONS

This application claims priority to and is a non-provisional application of U.S. Provisional Patent Application No. 61/922,257 filed Dec. 31, 2013, which is incorporated herein by reference in its entirety.

REFERENCE TO SEQUENCE LISTING

This application contains a Sequence Listing in computer readable form. The computer readable form is incorporated herein by reference.

FIELD

The disclosure relates to compositions and methods for increasing the performance of an animal. In one embodiment, the disclosure relates to compositions comprising direct-fed microbials and enzymes.

SUBMISSION OF SEQUENCE LISTING

The contents of the electronic submission of the text file Sequence Listing named AGP-37994 Sequence.Listing.txt, which was created Mar. 24, 2015, modified a first time Jun. 2, 2015, and modified a second time Jul. 2, 2015 and is 12.9 KB in size, is incorporated herein by reference in its entirety.

BACKGROUND

Animal feeds typically consist of a mixture of materials. For instance, a typical composition for a feed for poultry is 25% soybean meal. 50% corn, 20% byproducts suitable for animal feed and 5% minerals, vitamins, supplements and other feed additives. Feeds for other animals have different compositions, and soybean meal is one of the most important vegetable protein sources for animal feeds in general.

In order to achieve the most efficient growth of animals, the diet needs to be carefully controlled and thus the nutrient composition of the feedstuff is of high importance. However, natural raw materials have a high variation in nutrient composition. Thus, there is a tremendous need to identify ways to increase the performance of animals that is not wholly dependent on the raw materials of the feedstuff.

One approach to improving the health of animals is to alter the inhabitants of their gastrointestinal tract. Altering the inhabitants of the gastrointestinal tract of animals has been attempted by feeding direct-fed microbials to animals. A second approach to improving animal health of animals is to provide additional exogenous enzymes to the animals to aid in digestion, and increase the availability of nutrients. Methods and specific compositions that combine these two strategies would likely provide increased animal performance and would be a welcomed advance in the industry.

SUMMARY

Compositions and methods are disclosed for providing beneficial effects to animals, including but not limited to increasing performance of the animal. In one embodiment, the animal is poultry.

In one embodiment, the disclosure relates to a composition comprising one or more direct-fed microbials. In another embodiment, the disclosure relates to a composition comprising one or more direct-fed microbial and one or more enzymes.

In another embodiment, the disclosure relates to a composition comprising a multi-strain direct fed microbial comprising *B. subtilis* 27 (NRRL B-50105) or a strain having all of the identifying characteristics of the *B. subtilis* 27 (NRRL B-50105), *B. subtilis* strain BS2084 Accession No. NRRL B-50013 or a strain having all of the identifying characteristics of the BS2084 (NRRL B-50013). *B. subtilis* strain 3AP4 (PTA-6506) or a strain having all of the identifying characteristics of the 3AP4 ((PTA-6506), *B. licheniformis* 842 (NRRL B-50516) or a strain having all of the identifying characteristics of the *B. licheniformis* 842; and *B. licheniformis* 21 (NRRL B-50134) or a strain having all of the identifying characteristics of the *B. licheniformis* 21 (NRRL B-50134). In another embodiment, the composition further comprises exogenous feed enzymes. In still another embodiment, the composition comprises a xylanase, an amylase, and a protease.

In another embodiment, the disclosure relates to a method for increasing the performance of an animal comprising: administering to an animal an effective amount of a composition to increase performance, wherein the composition comprises *B. subtilis* 27 (NRRL B-50105); *B. subtilis* strain BS2084 Accession No. NRRL B-50013); *B. subtilis* strain 3AP4 (PTA-6506); *B. licheniformis* 842 (NRRL B-50516); and *B. licheniformis* 21 (NRRL B-50134), and a xylanase, amylase, and protease.

In another embodiment, the disclosure relates to a method for reducing the incidence of paw lesions comprising administering to poultry an effective amount of a composition to reduce paw lesions, wherein the composition comprises a multi-strain direct-fed microbial of *B. subtilis* 27 (NRRL B-50105); *B. subtilis* strain BS2084 Accession No. NRRL B-50013); *B. subtilis* strain 3AP4 (PTA-6506); *B. licheniformis* 842 (NRRL B-50516); and *B. licheniformis* 21 (NRRL B-50134), and a xylanase, amylase, and protease.

DETAILED DESCRIPTION

Unless defined otherwise, all technical and scientific terms used herein have the same meaning as commonly understood by one of ordinary skill in the art to which this disclosure belongs. Singleton, et al, DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure, which can be had by reference to the specification as a whole. Accordingly, the terms defined immediately below are more fully defined by reference to the specification as a whole.

It is noted that, as used in the specification and the appended claims, the singular forms "a," "an," and "the" include plural referents unless the context clearly dictates otherwise.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, melt index, temperature etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, "administer" is meant the action of introducing the strain, the exogenous feed enzyme and/or the strain and the exogenous feed enzyme to an environment.

As used herein, "amino acids" are referred to using the name of the amino acid, the three letter abbreviation or the single letter abbreviation.

As used herein, the term "amino acid sequence" is synonymous with the term "polypeptide." In some instances, the term "amino acid sequence" is synonymous with the term "peptide." In some instances, the term "amino acid sequence" is synonymous with the term "enzyme."

As used herein, the term "animal" includes but is not limited to human, mammal, amphibian, bird, reptile, pigs, cows, cattle, goats, horses, sheep, poultry, and other animals kept or raised on a farm or ranch, sheep, big-horn sheep, buffalo, antelope, oxen, donkey, mule, deer, elk, caribou, water buffalo, camel, llama, alpaca, rabbit, mouse, rat, guinea pig, hamster, ferret, dog, cat, and other pets, primate, monkey, ape, and gorilla. In some embodiments, the animals are poultry, including but not limited to broilers, chickens and turkeys.

By "at least one strain," is meant a single strain but also mixtures of strains comprising at least two strains of bacteria. By "a mixture of at least two strains," is meant a mixture of two, three, four, five, six or even more strains. In some embodiments of a mixture of strains, the proportions can vary from 1% to 99%. In certain embodiments, the proportion of a strain used in the mixture is at least 5%, 10%, 15%, 20%, 25%, 30%, 35%, 40%, 45%, 50%, 55%, 60%, 65%, 70%, 75%, 80%, 85%, 90%, or 95%. Other embodiments of a mixture of strains are from 25% to 75%. Additional embodiments of a mixture of strains are approximately 50% for each strain. When a mixture comprises more than two strains, the strains can be present in substantially equal proportions in the mixture or in different proportions.

As used herein, the term "compound feed" refers to a commercial feed in the form of a meal, a pellet, nuts, cake or a crumble. Compound feeds may be blended from various raw materials and additives. These blends are formulated according to the specific requirements of the target animal.

As used herein, "effective amount" is meant a quantity of DFM and/or exogenous enzymes to improve performance of an animal. Improvement in performance can be measured as described herein or by other methods known in the art. An effective amount can be administered to the animal by providing ad libitum access to feed containing the DFM and exogenous enzymes. The DFM and exogenous enzymes can also be administered in one or more doses.

As used herein, the term "feed" is used synonymously herein with "feedstuff."

As used herein, the term "feed component" refers to all or part of the feedstuff. Part of the feedstuff may mean one constituent of the feedstuff or more than one constituent of the feedstuff. e.g. 2 or 3 or 4. The term "feed component" encompasses a premix or premix constituents.

As used herein, the term "fodder" refers to any food that is provided to an animal (rather than the animal having to forage for it themselves). Fodder encompasses plants that have been cut. The term fodder includes hay, straw, silage, compressed and pelleted feeds, oils and mixed rations, and also sprouted grains and legumes.

As used herein, "performance" refers to the growth of an animal, such as a pig or poultry, measured by one or more of the following parameters: average daily gain (ADG), weight, scours, mortality, feed conversion, which includes both feed:gain and gain:feed, and feed intake. "An improvement in performance" or "improved performance" as used herein, refers to an improvement in at least one of the parameters listed under the performance definition.

As used herein, the term "protein" includes proteins, polypeptides, and peptides.

As used herein, "reducing the incidence of chicken paw lesions" includes but is not limited to reducing the incidence of chicken paw lesions by 3-5%, 5-10%, 10-20%, 20-30%, 30-40%, 40-50%, 50-60%, 60-70%, 70-80%, 80-90%, 90-95%, 96%, 97%, 98%, 99%, 100%, 100-125%, 125-150%, 150-200% or greater than 200%.

As used herein, a "variant" has at least 80% identity of genetic sequences with the disclosed strains using random amplified polymorphic DNA polymerase chain reaction (RAPD-PCR) analysis. The degree of identity of genetic sequences can vary. In some embodiments, the variant has at least 85%, 90%, 95%, 96%, 97%, 98%, or 99% identity of genetic sequences with the disclosed strains using RAPD-PCR analysis. Six primers that can be used for RAPD-PCR analysis include the following: Primer 1 (5'-GGTGCGGGAA-3') (SEQ ID No. 1), PRIMER 2 (5'-GTTTCGCTCC-3') (SEQ ID No. 2), PRIMER 3 (5'-GTAGACCCGT-3') (SEQ ID No. 3), PRIMER 4 (5'-AAGAGCCCGT-3') (SEQ ID No. 4), PRIMER 5 (5'-AACGCGCGCAAC-3') (SEQ ID No. 5), PRIMER 6 (5'-CCCGTCAGCA-3') (SEQ ID No. 6). RAPD analysis can be performed using Ready-to-Go™ RAPD Analysis Beads (Amersham Biosciences, Sweden), which are designed as pre-mixed, pre-dispensed reactions for performing RAPD analysis.

The disclosure is directed to compositions and methods for improving performance of an animal. In another embodiment, the disclosure is directed to compositions and methods for increasing performance of poultry. In yet another embodiment, composition and methods disclosed herein increase performance of broilers.

Certain *Bacillus* strains can be used to increase performance measures of an animal. In another embodiment, *Bacillus* strains in combination with one or more exogenous feed enzymes can be used to increase performance measures of an animal. In yet another embodiment, a multiple-strain direct-fed microbial (DFM) in combination with one or more exogenous feed enzymes is administered to an animal.

In one embodiment, *Bacillus* strains useful in the composition and methods disclosed herein include but are not limited to *B. subtilis* and *B. licheniformis*. In another embodiment, exogenous feed enzymes include but are not limited to xylanase, amylase and protease.

I. Direct Fed Microbials

A. Strains

Direct-fed microbials (DFMs) are bacteria that provide animals positive effects, including, but not limited to, increasing performance. Performance measures include but are not limited to such parameters as average daily feed intake, average daily weight gain, total weight gain, European production factor, feed conversion, which includes both feed:gain and gain:feed, feed efficiency, mortality, and actual production costs. In addition, performance measures also include the incidence of poultry paw lesions and the economic value of poultry feet.

In one embodiment, the disclosure relates to compositions comprising or consisting of or consisting essentially of one or more bacterial strains. As used herein, a composition may be a liquid, a heterogeneous mixture, a homogeneous mixture, a powder, a solution, a dispersion, lyophilized, freeze-dried, or any combination thereof.

Strains useful in the compositions and methods of the disclosure include *Bacillus* strains, including, but not limited to *B. subtilis* and *B. licheniformis*. In one embodiment, the *Bacillus subtilis* strains include but are not limited to *B. subtilis* strain 27 (NRRL B-50105), *B. subtilis* strain 2084 (NRRL B-50013), and *B. subtilis* strain 3A-P4 (PTA-6506).

In another embodiment, the *B. licheniformis* strains include but are not limited to *B. licheniformis* strain 842 (NRRL B-50516) and *B. licheniformis* strain 21 (NRRL B-50134).

In one embodiment, the *Bacillus subtilis* strain is *B. subtilis* 27 (NRRL B-50105) or a strain having all of the identifying characteristics of the *B. subtilis* 27 (NRRL B-50105).

In one embodiment, the *Bacillus subtilis* strain is *B. subtilis* strain BS2084 Accession No. NRRL B-50013 or a strain having all of the identifying characteristics of the BS2084 (NRRL B-50013).

In yet another embodiment, the *Bacillus subtilis* strain is *B. subtilis* strain 3AP4 (PTA-6506) or a strain having all of the identifying characteristics of the 3AP4 ((PTA-6506).

In still another embodiment, the *Bacillus licheniformis* strain is *B. licheniformis* 842 (NRRL B-50516) or a strain having all of the identifying characteristics of the *B. licheniformis* 842;

In another embodiment, the *B. licheniformis* strain is *B. licheniformis* 21 (NRRL B-50134) or a strain having all of the identifying characteristics of the *B. licheniformis* 21 (NRRL B-50134).

In one embodiment, the composition or DFM is a mixture of at least two strains selected from the group consisting of *B. subtilis* strain 27 (NRRL B-50105), *B. subtilis* strain 2084 (NRRL B-50013), *B. subtilis* strain 3A-P4 (PTA-6506). *B. licheniformis* strain 842 (NRRL B-50516) and *B. licheniformis* strain 21 (NRRL B-50134).

In yet another embodiment, the composition or DFM is a mixture of *B. subtilis* strain 27 (NRRL B-50105) or a strain having all of the identifying characteristics of the *B. subtilis* 27 (NRRL B-50105); *B. subtilis* strain BS2084 Accession No. NRRL B-50013 or a strain having all of the identifying characteristics of the BS2084 (NRRL B-50013); *B. subtilis* strain 3AP4 (PTA-6506) or a strain having all of the identifying characteristics of the 3AP4 ((PTA-6506); *B. licheniformis* 842 (NRRL B-50516) or a strain having all of the identifying characteristics of the *B. licheniformis* 842; and *B. licheniformis* 21 (NRRL B-50134) or a strain having all of the identifying characteristics of the *B. licheniformis* 21 (NRRL B-50134).

In yet another embodiment, the composition or DFM is a mixture of *B. subtilis* 27 (NRRL B-50105) or a variant of *B. subtilis* 27 (NRRL B-50105); *B. subtilis* strain BS2084 Accession No. NRRL B-50013 or a variant of BS2084 (NRRL B-50013); *B. subtilis* strain 3AP4 (PTA-6506) or a variant of 3AP4 ((PTA-6506); *B. licheniformis* 842 (NRRL B-50516) or a variant of *B. licheniformis* 842; and *B. licheniformis* 21 (NRRL B-50134) or a variant of *B. licheniformis* 21 (NRRL B-50134).

For purposes of this disclosure, a "biologically pure strain" means a strain containing no other bacterial strains in quantities sufficient to interfere with replication of the strain or to be detectable by normal bacteriological techniques. "Isolated" when used in connection with the organisms and cultures described herein includes not only a biologically pure strain, but also any culture of organisms that is grown or maintained other than as it is found in nature.

B. Deposits Under the Budapest Treaty

On Jul. 1, 2011, *B. licheniformis* strain 842 was deposited at Agricultural Research Service Culture Collection (NRRL), 1815 North University Street, Peoria, Ill., 61604 and given accession number NRRL B-50516.

On Apr. 15, 2008, *B. licheniformis* strain 21 was deposited at NRRL and given accession number NRRL B-50134.

On Jan. 24, 2008, *B. subtilis* strain 27 was deposited at NRRL and given accession number NRRL B-50105.

On Mar. 8, 2007, *B. subtilis* strain 2084 was deposited at NRRL and given accession number NRRL B-50013.

On Jan. 12, 2005, *B. subtilis* strain 3A-P4 was deposited at the American Type Culture Collection (ATCC), 10801 University Blvd., Manassas, Va. 20110-2209 and given accession numbers PTA-6506 (3A-P4).

All of the deposits were made under the provisions of the Budapest Treaty on the International Recognition of the Deposit of Microorganisms for the Purposes of Patent Procedure.

Agtech and Danisco USA Inc. of W227 N752 Westmound Dr. Waukesha, Wis. 53186, USA authorize DuPont Nutrition Biosciences ApS (formerly Danisco A/S) of Langebrogade I. PO Box 17, DK-1001, Copenhagen K, Denmark to refer to these deposited biological materials in this patent application and have given unreserved and irrevocable consent to the deposited material being made available to the public.

C. Methods of Culturing Strains

The *Bacillus* strains can be produced by fermentation of the bacterial strains. Fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

The count of the culture can then be determined. A colony forming unit (CFU) is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

In one embodiment, the *Bacillus* strains disclosed herein can be fermented between $5\times10^3$ CFU/ml to about $4\times10^{12}$ CFU/ml level.

In one embodiment, the *Bacillus* strains disclosed herein can be fermented between $5\times10^2$ CFU/ml to about $4\times10^9$ CFU/ml. In at least one embodiment, a level of $2\times10^9$ CFU/ml is used. The bacteria are harvested by centrifugation, and the supernatant is removed. The supernatant can be used in the methods described herein. In at least some embodiments, the bacteria are pelleted. In at least some embodiments, the bacteria are freeze-dried. In at least some embodiments, the bacteria are mixed with a carrier. However, it is not necessary to freeze-dry the *Bacillus* before using them. The strains can also be used with or without preservatives, and in concentrated, unconcentrated, or diluted form.

In one embodiment, the disclosure relates to a biologically pure culture comprising, consisting of, or consisting essentially of one or more *Bacillus* strains disclosed herein at a concentration of about $5\times10^2$ CFU/ml to about $5\times10^9$ CFU/ml.

In one embodiment, the disclosure relates to a culture comprising, consisting of, or consisting essentially of one or more *Bacillus* strains disclosed herein at a concentration of $5\times10^2$ CFU/ml.

In one embodiment, the disclosure relates to a culture comprising, consisting of, or consisting essentially of one or more *Bacillus* strains disclosed herein at a concentration of $5\times10^3$ CFU/ml.

D. Methods of Preparing a DFM

A composition including one or more strain(s) described herein is provided. The composition can be fed to an animal as a direct-fed microbial (DFM). One or more carrier(s) or other ingredients can be added to the DFM. The DFM may be presented in various physical forms, for example, as a top dress, as a water soluble concentrate for use as a liquid drench or to be added to a milk replacer, gelatin capsule, or gels. In one embodiment of the top dress form, a freeze-dried bacteria fermentation product is added to a carrier, such as whey, maltodextrin, sucrose, dextrose, limestone (calcium carbonate), rice hulls, yeast culture, dried starch, and/or sodium silico aluminate. In one embodiment of the water soluble concentrate for a liquid drench or milk replacer supplement, freeze-dried lactic acid bacteria fermentation product is added to a water soluble carrier, such as whey, maltodextrin, sucrose, dextrose, dried starch, sodium silico aluminate, and a liquid is added to form the drench or the supplement is added to milk or a milk replacer. In one embodiment of the gelatin capsule form, freeze-dried bacteria fermentation product is added to a carrier, such as whey, maltodextrin, sugar, limestone (calcium carbonate), rice hulls, yeast culture dried starch, and/or sodium silico aluminate. In one embodiment, the bacteria and carrier are enclosed in a degradable gelatin capsule. In one embodiment of the gels form, freeze-dried fermentation product is added to a carrier, such as vegetable oil, sucrose, silicon dioxide, polysorbate 80, propylene glycol, butylated hydroxyanisole, citric acid, ethoxyquin, and/or artificial coloring to form the gel.

The strain(s) may optionally be admixed with a dry formulation of additives including but not limited to growth substrates, enzymes, sugars, carbohydrates, extracts and growth promoting micro-ingredients. The sugars could include the following: lactose: maltose; dextrose; maltodextrin; glucose; fructose; mannose; tagatose; sorbose; raffinose; and galactose. The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and Tween 80, ranging from 1-5%. The carbohydrates could include mannitol, sorbitol, adonitol and arabitol. The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and manganese, ranging from 0.25-1.0%.

To prepare DFMs described herein, the culture(s) and carrier(s) (where used) can be added to a ribbon or paddle mixer and mixed for about 15 minutes, although the timing can be increased or decreased. The components are blended such that a uniform mixture of the cultures and carriers result. The final product is preferably a dry, flowable powder. The strain(s) can then be added to animal feed or a feed premix, added to an animal's water, or administered in other ways known in the art. A feed for an animal can be supplemented with one or more strain(s) described herein or with a composition described herein.

II. Exogenous Enzymes

Supplemental enzymes can be used as additives to animal feed, particularly poultry and swine feeds, as a means to improve nutrient utilization and performance characteristics.

In one embodiment, the disclosure relates to a composition comprising one or more DFM and one or more exogenous feed enzymes. In another embodiment, the disclosure relates to a composition comprising, consisting of, or consisting essentially of a multi-strain DFM and one or more exogenous feed enzymes.

In yet another embodiment, the disclosure relates to composition comprising a multi-strain DFM comprising *B. subtilis* 27 (NRRL B-50105) or a strain having all of the identifying characteristics of the *B. subtilis* 27 (NRRL B-50105); *B. subtilis* strain BS2084 Accession No NRRL B-50013 or a strain having all of the identifying characteristics of the BS2084 (NRRL B-50013); *B. subtilis* strain 3AP4 (PTA-6506) or a strain having all of the identifying characteristics of the 3AP4 ((PTA-6506); *B. licheniformis* 842 (NRRL B-50516) or a strain having all of the identifying characteristics of the *B. licheniformis* 842; and *B. licheniformis* 21 (NRRL B-50134) or a strain having all of the identifying characteristics of the *B. licheniformis* 21 (NRRL B-50134) and one or more exogenous feed enzymes.

In yet another embodiment, the disclosure relates to composition comprising a multi-strain DFM comprising *B. subtilis* strain 27 (NRRL B-50105), *B. subtilis* strain 2084 (NRRL B-50013). *B. subtilis* strain 3A-P4 (PTA-6506), *B. licheniformis* strain 842 (NRRL B-50516) and *B. licheniformis* strain 21 (NRRL B-50134) and one or more exogenous feed enzymes.

In one embodiment, the exogenous feed enzymes include but are not limited to xylanase, amylase and protease.

In one embodiment, the exogenous feed enzymes are xylanase and amylase. In another embodiment, the exogenous feed enzymes are xylanase and protease. In yet another embodiment, the exogenous feed enzymes are amylase and protease. In still another embodiment, the composition comprises a feed additive.

A. Xylanase

Xylanase is the name given to a class of enzymes that degrade the linear polysaccharide β-1,4-xylan into xylose, thus breaking down hemicellulose, one of the major components of plant cell walls. Xylanases, e.g., endo-β-xylanases (EC 3.2.1.8) hydrolyze the xylan backbone chain.

In one embodiment, the disclosure relates to a composition comprising one or more strains disclosed herein and one or more xylanase.

In one embodiment, the xylanase may be any commercially available xylanase. Suitably the xylanase may be an endo-1,4-P-d-xylanase (classified as E.G. 3.2.1.8) or a 1,4β-xylosidase (classified as E.G. 3.2.1.37).

In one embodiment, the disclosure relates to a DFM in combination with an endoxylanase, e.g. an endo-1,4-P-d-xylanase, and another enzyme.

All E.C. enzyme classifications referred to herein relate to the classifications provided in Enzyme Nomenclature—Recommendations (1992) of the nomenclature committee of the International Union of Biochemistry and Molecular Biology—ISBN 0-12-226164-3, which is incorporated herein by reference in its entirety.

In another embodiment, the xylanase may be a xylanase from *Bacillus, Trichodermna, Therinomyces, Aspergillus* and *Penicillium*.

In still another embodiment, the xylanase may be the xylanase in Axtra XAP® or Avizyme 1502®, both commercially available products from Danisco A/S.

In one embodiment, the xylanase may be a mixture of two or more xylanases.

In still another embodiment, the xylanase is an endo-1,4-β-xylanase or a 1,4-β-xylosidase. In yet another embodiment, the xylanase is from an organism selected from the group consisting of: *Bacillus, Trichoderma, Thermomyces, Aspergillus, Penicillium*, and *Humicola*.

In yet another embodiment, the xylanase may be one or more of the xylanases or one or more of the commercial products recited in Table 1.

TABLE 1

Representative examples of commercial xylanases.

| Commercial Name ® | Company | Xylanase type | Xylanase source |
|---|---|---|---|
| Allzyme PT | Alltech | endo-1,4-β-xylanase | *Aspergillus Niger* |
| Amylofeed | Andrés Pintaluba S.A | endo-1,4-β-xylanase | *Aspergillus Niger (phoenicis)* |
| Avemix 02 CS | Aveve | endo-1,4-β-xylanase | *Trichoderma reesei* |
| AveMix XG 10 | Aveve, NL | endo-1,4-β-xylanase | *Trichoderma reesei* |
| Avizyme 1100 | Danisco | endo-1,4-β-xylanase | *Trichoderma longibrachiatum* |
| Avizyme 1110 | Danisco | endo-1,4-β-xylanase | *Trichoderma longibrachiatum* |
| Avizyme 1202 | Danisco | endo-1,4-β-xylanase | *Trichoderma longibrachiatum* |
| Avizyme 1210 | Danisco | endo-1,4-β-xylanase | *Trichoderma longibrachiatum* |
| Avizyme 1302 | Danisco | endo-1,4-β-xylanase | *Trichoderma longibrachiatum* |
| Avizyme 1500 | Danisco | endo-1,4-β-xylanase | *Trichoderma longibrachiatum* |
| Avizyme 1505 | Danisco | endo-1,4-β-xylanase | *Trichoderma longibrachiatum* |
| Avizyme SX | Danisco | endo-1,4-β-xylanase | *Trichoderma longibrachiatum* |
| Belfeed MP 100 | Beldem | endo-1,4-β-xylanase | *Bacillus subtilis* |
| Biofeed Plus | DSM | endo-1,4-β-xylanase | *Humicola insolens* |
| Danisco Glycosidase (TPT/L) | Danisco Animal Nutrition | endo-1,4-β-xylanase | *Trichoderma reesei* |
| Danisco Xylanase | Danisco | endo-1,4-β-xylanase | *Trichoderma reesei* |
| Econase XT | AB Vista | endo-1,4-β-xylanase | *Trichoderma reesei* |
| Endofeed ® DC | Andrés Pintaluba S.A. | endo-1,4-β-xylanase | *Aspergillus Niger* |
| Feedlyve AXL | Lyven | endo-1,4-β-xylanase | *Trichoderma longibrachiatum* |
| Grindazym GP | Danisco | endo-1,4-β-xylanase | *Aspergillus Niger* |
| Grindazym GV | Danisco | endo-1,4-β-xylanase | *Aspergillus Niger* |
| Hostazym X | Huvepharma | endo-1,4-β-xylanase | *Trichoderma longibrachiatum* |
| Kemzyme Plus Dry | Kemin | endo-1,4-β-xylanase | *Trichoderma viride* |
| Kemzyme Plus Liquid | Kemin | endo-1,4-β-xylanase | *Trichoderma viride* |
| Kemzyme W dry | Kemin | endo-1,4-β-xylanase | *Trichoderma viride* |
| Kemzyme W liquid | Kemin | endo-1,4-β-xylanase | *Trichoderma viride* |
| Natugrain | BASF | endo-1,4-β-xylanase | *Trichoderma longibrachiatum* |
| Natugrain TS Plus | BASF | endo-1,4-β-xylanase | *Aspergillus Niger* |
| Natugrain Wheat | BASF | endo-1,4-β-xylanase | *Aspergillus Niger* |
| Natugrain ® TS/L | BASF | endo-1,4-β-xylanase | *Aspergillus Niger* |
| Natuzyme | Bioproton | endo-1,4-β-xylanase | *Trichoderma longibrachiatum/ Trichoderma reesei* |
| Porzyme 8100 | Danisco | endo-1,4-β-xylanase | *Trichoderma longibrachiatum* |
| Porzyme 8300 | Danisco | endo-1,4-β-xylanase | *Trichoderma longibrachiatum* |
| Porzyme 9102 | Danisco | endo-1,4-β-xylanase | *Trichoderma longibrachiatum* |
| Porzyme 9310/Avizyme 1310 | Danisco | endo-1,4-β-xylanase | *Trichoderma longibrachiatum* |

TABLE 1-continued

Representative examples of commercial xylanases.

| Commercial Name ® | Company | Xylanase type | Xylanase source |
|---|---|---|---|
| Porzyme tp 100 | Danisco | endo-1,4-β-xylanase | *Trichoderma longibrachiatum* |
| Ronozyme AX | DSM | endo-1,4-β-xylanase | *Thermomyces lanuginosus* gene expressed in *Aspergillus oryzae* |
| Ronozyme WX | DSM/Novozymes | endo-1,4-β-xylanase | *Thermomyces lanuginosus* gene expressed in *Aspergillus oryzae* |
| Rovabio Excel | Adisseo | endo-1,4-β-xylanase | *Penicillium funiculosum* |
| Roxazyme G2 | DSM/Novozymes | endo-1,4-β-xylanase | *Trichoderma longibrachiatum* |
| Safizym X | Le Saffre | endo-1,4-β-xylanase | *Trichoderma longibrachiatum* |
| Xylanase | Lyven | endo-1,4-β-xylanase | *Trichoderma longibrachiatum* |

In one embodiment, the xylanase is a purified xylanase described in U.S. Pat. No. 5,902,581, which is incorporated by reference in its entirety. The xylanase in U.S. Pat. No. 5,902,581 is characterized by the following physical properties: a pH optimum of about 3.6 to 4.2, a molecular weight of about 50-55 kD as determined by gel filtration, pH of about 6.0-6.5, and a temperature optimum of about 70-80° C. Preferably, the xylanase is derived from *Acidothermus* sp., more preferably from *Acidothermus cellulolyticus* and most preferably from *Acidothermus cellulolyticus* ATCC 43068.

In one embodiment, the disclosure relates to a composition comprising a multi-strain DFM and xylanase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 xylanase units/g of composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, and greater than 8000 xylanase units/g composition.

It will be understood that one xylanase unit (XU) is the amount of enzyme that releases 0.5 μmol of reducing sugar equivalents (as xylose by the Dinitrosalicylic acid (DNS) assay-reducing sugar method) from a oat-spelt-xylan substrate per min at pH 5.3 and 50° C. (Bailey, M J. Biely, P. and Poutanen, K., Journal of Biotechnology, Volume 23, (3), May 1992, 257-270).

B. Amylase

Amylase is a class of enzymes capable of hydrolysing starch to shorter-chain oligosaccharides, such as maltose. The glucose moiety can then be more easily transferred from maltose to a monoglyceride or glycosylmonoglyceride than from the original starch molecule.

The term amylase includes α-amylases (E.G. 3.2.1.1), G4-forming amylases (E.G. 3.2.1.60), β-amylases (E.G. 3.2.1.2) and γ-amylases (E.C. 3.2.1.3).

Amylases may be of bacterial or fungal origin, or chemically modified or protein engineered mutants.

In one embodiment, the disclosure relates to a composition comprising one or more strains disclosed herein and one or more amylase.

In still another embodiment, the disclosure relates to a composition comprising one or more strains disclosed herein, one or xylanase, and one or more amylase.

In one embodiment, the amylase may be a mixture of two or more amylases. In another embodiment, the amylase may be an amylase, e.g. an α-amylase, from *Bacillus licheniformis* and an amylase, e.g. an α-amylase, from *Bacillus amyloliquefaciens*.

In one embodiment, the α-amylase may be the α-amylase in Axtra XAP® or Avizyme 1502®, both commercially available products from Danisco A/S.

In yet another embodiment, the amylase may be a pepsin resistant α-amylase, such as a pepsin resistant *Trichoderma* (such as *Trichoderma reesei*) alpha amylase. A suitably pepsin resistant α-amylase is taught in UK application number 101 1513.7 (which is incorporated herein by reference) and PCT/IB2011/053018 (which is incorporated herein by reference).

In one embodiment, the amylase may be a pepsin resistant α-amylase comprising the amino acid sequence of SEQ ID NO. 7:

```
                                          (SEQ ID NO. 7)
Ala Asn Leu Asn Gly Thr Leu Met Gln Tyr Phe Gln

Trp Tyr Met Pro Asn Asp Gly Gln His Trp Lys Arg

Leu Gln Asn Asp Ser Ala Tyr Leu Ala Gln His Gly

Ile Thr Ala Val Trp Ile Pro Pro Ala Tyr Lys Gly

Thr Ser Gln Ala Asp Val Gly Tyr Gly Ala Tyr Asp

Leu Tyr Asp Leu Gly Glu Phe His Gln Lys Gly Thr

Val Arg Thr Lys Tyr Gly Thr Lys Gly Glu Leu Gln

Ser Ala Ile Lys Ser Leu His Ser Arg Asp Ile Asn

Val Tyr Gly Asp Val Val Ile Asn His Lys Gly Gly

Ala Asp Ala Thr Gln Asp Val Thr Ala Val Glu Val

Asp Pro Ala Asp Arg Asn Arg Val Ile Ser Gly Glu

His Leu Ile Lys Ala Trp Thr His Phe His Phe Pro

Gly Arg Gly Ser Thr Tyr Ser Asp Phe Lys Trp His

Trp Tyr His Phe Asp Gly Thr Asp Trp Asp Glu Ser

Arg Lys Leu Asn Arg Ile Tyr Lys Phe Gln Gly Lys

Ala Trp Asp Trp Gln Val Ser Asn Gln Asn Gly Asn

Tyr Asp Tyr Leu Met Tyr Ala Asp Ile Asp Tyr Asp
```

His Pro Asp Val Ala Ala Glu Ile Lys Arg Trp Gly

Thr Trp Tyr Ala Asn Glu Len Gln Leu Asp Gly Phe

Arg Leu Asp Ala Val Lys His Ile Lys Phe Ser Phe

Leu Arg Asp Trp Val Asn His Val Arg Glu Lys Thr

Gly Lys Gln Met Phe Thr Val Ala Gln Tyr Trp Gln

Asn Asp Len Gly Ala Leu Glu Asn Tyr Leu Asn Lys

Thr Asn Phe Asn His Set Val Phe Asp Val Pro Leu

His Tyr Gln Phe His Ala Ala Ser Thr Gln Gly Gly

Gly Tyr Asp Met Arg Lys Leu Leu Asn Gly Thr Val

Val Ser Lys His Pro Len Lys Set Val Thr Phe Val

Asp Asn His Asp Thr Gln Pro Gly Gln Ser Leu Glu

Ser Thr Val Gln Thr Trp Phe Lys Pro Leu Ala Tyr

Ala Phe Ile Leu Thr Arg Gln Ser Gly Tyr Pro Gln

Val Phe Tyr Gly Asp Met Tyr Gly Thr Lys Gly Asp

Ser Gln Arg Gln Ile Pro Ala Leu Lys His Lys Ile

Gln Pro Ile Leu Lys Ala Arg Lys Gln Tyr Ala Tyr

Gly Ala Gln His Asp Tyr Phe Asp His His Asp Ile

Val Gly Trp Thr Arg Gln Gly Asp Ser Ser Val Ala

Asn Ser Gly Leu Ala Ala Leu Ile Thr Asp Gly Pro

Gly Gly Ala Lys Arg Met Tyr Val Gly Arg Gln Asn

Ala Gly Gln Thr Trp His Asp Ile Thr Gly Asn Arg

Ser Gln Pro Val Val Ile Asn Ser Glu Gly Trp Gly

Gln Phe His Val Asn Gly Gly Ser Val Set Ile Tyr

Val Gln Arg.

In another embodiment, the amylase may be a pepsin resistant α-amylase comprising the amino acid sequence of SEQ ID NO. 9:

(SEQ ID No. 9)
Met Lys Leu Arg Tyr Ala Leu Pro Leu Leu Leu Gln

Len Ser Leu Pro Val Leu Ser Ala Asp Thr Ala Ala

Trp Arg Ser Arg Thr Ile Tyr Phe Ala Leu Thr Asp

Arg Ile Ala Arg Gly Ser Gly Asp Thr Gly Gly Ser

Ala Cys Gly Asn Leu Gly Asp Tyr Cys Gly Gly Thr

Phe Gln Gly Leu Gln Ser Lys Leu Asp Tyr Ile Lys

Gly Met Gly Phe Asp Ala Ile Trp Ile Thr Pro Val

Val Thr Ser Asp Asp Gly Gly Tyr His Gly Tyr Trp

Ala Gln Asp Ile Asp Ser Ile Asn Ser His Tyr Gly

Ser Ala Asp Asp Leu Lys Ser Leu Val Asn Ala Ala

His Ser Lys Gly Phe Tyr Met Met Val Asp Val Val

Ala Asn His Met Gly Tyr Ala Asn Ile Ser Asp Asp

Ser Pro Ser Pro Leu Asn Gln Ala Ser Ser Tyr His

Pro Glu Cys Asp Ile Asp Tyr Asn Asn Gln Thr Ser

Val Gln Asn Cys Trp Ile Ser Gly Leu Pro Asp Leu

Asn Thr Gln Ser Ser Thr Ile Arg Ser Leu Tyr Gln

Asp Trp Val Ser Asn Leu Val Ser Thr Tyr Gly Phe

Asp Gly Val Arg Ile Asp Thr Val Lys His Val Glu

Gln Asp Tyr Trp Pro Gly Phe Val Asn Ala Thr Gly

Val Tyr Cys Ile Gly Glu Val Phe Asp Gly Asp Pro

Asn Tyr Leu Leu Pro Tyr Ala Ser Leu Met Pro Gly

Leu Leu Asn Tyr Ala Ile Tyr Tyr Pro Met Thr Arg

Phe Phe Leu Gln Gln Gly Ser Ser Gln Asp Met Val

Asn Met His Asp Gln Ile Gly Ser Met Phe Pro Asp

Pro Thr Ala Leu Gly Thr Phe Val Asp Asn His Asp

Asn Pro Arg Phe Leu Ser Ile Lys Asn Asp Thr Ala

Leu Leu Lys Asn Ala Leu Thr Tyr Thr Ile Leu Ser

Arg Gly Ile Pro Ile Val Tyr Tyr Gly Thr Glu Gln

Ala Phe Ser Gly Gly Asn Asp Pro Ala Asn Arg Gln

Asp Leu Trp Arg Ser Gly Phe Asn Ala Gln Ser Asp

Met Tyr Asp Ala Ile Ser Lys Leu Thr Tyr Ala Lys

His Ala Val Gly Gly Leu Ala Asp Asn Asp His Lys

His Leu Tyr Val Ala Asp Thr Ala Tyr Ala Phe Ser

Arg Ala Gly Gly Asn Met Val Ala Leu Thr Thr Asn

Ser Gly Ser Gly Ser Ser Ala Gln His Cys Phe Gly

Thr Gln Val Pro Asn Gly Arg Trp Gln Asn Val Phe

Asp Glu Gly Asn Gly Pro Thr Tyr Ser Ala Asp Gly

Asn Gly Gln Leu Cys Leu Asn Val Ser Asn Gly Gln

Pro Ile Val Leu Leu Ser Ser.

In another embodiment, the amylase may be a pepsin resistant α-amylase comprising the amino acid sequence as set forth in SEQ ID No. 7 or SEQ ID No. 9 with one or several amino acid additions/insertions, deletions or substitutions.

In another embodiment, the amylase may be a pepsin resistant α-amylase having at least 85% or at least 90%, or at least 95%, or at least 97%, or at least 98% or at least 99% identity to SEQ ID No. 7.

In another embodiment, the amylase may be a pepsin resistant α-amylase having at least 70%, or at least 75%, or at least 80%, or at least 85%, or at least 90%, or at least 95%, 97%, 98% or 99% identity to SEQ ID No. 9.

In yet another embodiment, the amylase may be a pepsin resistant α-amylase produced by expression of a nucleotide sequence comprising the sequence of SEQ ID No. 8:

(SEQ ID NO. 8)
gcaaatctta atgggacgct gatgcagtat tttgaatggt acatgcccaa tgacggccaa cattggaagc gtttgcaaaa -continued

```
cgactcggca tatttggctg aacacggtat tactgccgtc
tggattcccc cggcatataa gggaacgagc caagcggatg
tgggctacgg tgcttacgac ctttatgatt taggggagtt
tcatcaaaaa gggacggttc ggacaaagta cggcacaaaa
ggagagctgc aatctgcgat caaaagtctt cattcccgcg
acattaacgt ttacggggat gtggtcatca accacaaagg
cggcgctgat gcgaccgaag atgtaaccgc ggttgaagtc
gatcccgctg accgcaaccg cgtaatttca ggagaacacc
taattaaagc ctggacacat tttcattttc cggggcgcgg
cagcacatac agcgatttta aatggcattg gtaccatttt
gacggaaccg attgggacga gtcccgaaag ctgaaccgca
tctataagtt tcaaggaaag gcttgggatt gggaagtttc
caatgaaaac ggcaactatg attatttgat gtatgccgac
atcgattatg accatcctga tgtcgcagca gaaattaaga
gatgggcac ttggtatgcc aatgaactgc aattggacgg
tttccgtctt gatgctgtca aacacattaa attttctttt
ttgcgggatt gggttaatca tgtcaggaa aaaacgggga
aggaaatgtt tacggtagct gaatattggc agaatgactt
gggcgcgctg gaaaactatt tgaacaaaac aaattttaat
cattcagtgt ttgacgtgcc gcttcattat cagttccatg
ctgcatcgac acaggaggc ggctatgata tgaggaaatt
gctgaacggt acggtcgttt ccaagcatcc gttgaaatcg
gttacatttg tcgataacca tgatacacag ccggggcaat
cgcttgagtc gactgtccaa acatggttta agccgcttgc
ttacgctttt attctcacaa gggaatctgg atacctcag
gttttctacg gggatatgta cgggacgaaa ggagactccc
agcgcgaaat tcctgccttg aaacacaaaa ttgaaccgat
cttaaaagcg agaaaacagt atgcgtacgg agcacagcat
gattatttcg accaccatga cattgtcggc tggacaaggg
aaggcgacag aattcaggtt tggcggcatt aataacagac
ggaccggtg gggcaaagcg aatgtatgtc ggccggcaaa
acgccggtga gacatggcat gacattaccg gaaaccgttc
ggagccggtt gtcatcaatt cggaaggctg gggagagttt
cacgtaaacg gcgggtcggt ttcaatttat gttcaaagat
ga.
```

In yet another embodiment, the amylase may be a pepsin resistant α-amylase which is produced by expression of a nucleotide sequence comprising the sequence of SEQ ID No. 10:

```
                                      (SEQ ID No. 10)
atgaagctcc ggtacgctct cccgctgctc ttgcagctct
ctttgccggt cctctccgca gacaccgccg cctggaggtc
ccgcaccatc tactttgccc tgacagaccg catcgctcgt
ggaagcggtg acacgggggg cagtgcgtgt gggaacctgg
gggactactg cggtggcacg ttccagggct tggagagcaa
gttggactac atcaagggca tgggattcga tgccatctgg
atcacacctg ttgtgacgag tgatgatggg ggctaccatg
gctattgggc ggaggacatc gactccatca actctcatta
tggctctgcg gacgatctca agagtctcgt caacgccgcg
catgcaaagg gcttctatat gatggtggac gtcgtggcca
accacatggg ctacgccaat atctctgacg atagtccctc
tccactgaac caggcctcgt cgtatcaccc cgagtgtgat
atcgactaca acaaccaaac cagcgtcgag aactgctgga
tcagcggcct cccggatctc aatacgcaga gctcaaccat
ccagcagggc taccaggact gggtctccaa cctcgtgtcc
acgtacggct tcgacggcgt ccgcatcgac accgtcaagc
acgtcgagca agactactgg cccggcttcg tcaacgccac
cggcgtctac tgcatcggcg aggtctttga cggagaccca
aactacctgc tgccctacgc cagcctcatg ccgggcctgc
tcaactacgc catctactac cccatgacgc gcttcttcct
ccagcagggc tcctcgcagg acatggtcaa catgcacgac
cagatcggca gcatgttccc cgacccgacc gcgctcggca
cctttgtcga caaccacgac aacccgcgct tcctgagcat
caagaacgac acggccctgc tcaagaacgc gctgacgtac
accatcctct cgcgcggcat ccccatcgtc tactacggca
ccgagcaggc cttctcgggc ggcaacgacc cggccaacag
ggaggacctc tggcgcagcg gcttcaacgc ccagtccgac
atgtacgacg ccatctccaa gctcacctac gccaagcacg
ccgtcggcgg cctcgccgac aacgaccaca agcacctgta
cgtcgccgac acggcctacg ccttcagccg cgccggcggc
aacatggtgg ccctgaccac caacagcggc agcgggagct
cggcccagca ctgcttcggc acgcaggtgc ccaacggccg
ctggcagaat gtctttgacg agggcaatgg gccgacgtat
tccgccgacg gcaacggcca gctttgcttg aatgtgtcca
acggtcagcc cattgtcttgctgtcttcgt ga.
```

In yet another embodiment, the amylase may be a pepsin resistant α-amylase that is produced by expression of a nucleotide sequence which differs from SEQ ID No. 8 or SEQ ID No. 10 due to the degeneracy of the genetic code.

In still another embodiment, the amylase may be a pepsin resistant α-amylase that is produced by expression of a nucleotide sequence that differs from SEQ ID No. 8 or SEQ ID No. 10 by one or several nucleotide additions/insertions, deletions or substitutions.

In another embodiment, the amylase may be a pepsin resistant α-amylase that is produced by expression of a nucleotide sequence that has at least 70%, or at least 75%, or at least 80%, or at least 85%, or at least 90%, or at least 95%, or at least 97%, or at least 98% or at least 99% identity to SEQ ID No. 8 or SEQ ID No. 10.

The pepsin resistant alpha amylase may also be encoded by a nucleotide sequence that hybridizes to SEQ ID No. 8 or SEQ ID No. 10 under stringent or highly stringent conditions.

In one preferred embodiment the amylase for use in the present invention may be one or more of the amylases in one or more of the commercial products below:

TABLE 2

Representative examples of commercial amylases.

| Commercial product ® | Company | Amylase type | Amylase source |
|---|---|---|---|
| Amylofeed | Andrés Pintaluba S.A | alpha amylase | *Aspergillus oryzae* |
| Avizyme 1500 | Danisco | alpha amylase | *Bacillus amyloliquefaciens* |
| Avizyme 1505 | Danisco | alpha amylase | *Bacillus amyloliquefaciens* |
| Kemzyme Plus Dry | Kemin | alpha-amylase | *Bacillus amyloliquefaciens* |
| Kemzyme Plus Liquid | Kemin | alpha-amylase | *Bacillus amyloliquefaciens* |
| Kemzyme W dry | Kemin | alpha-amylase | *Bacillus amyloliquefaciens* |
| Kemzyme W liquid | Kemin | alpha-amylase | *Bacillus amyloliquefaciens* |
| Natuzyme | Bioproton | alpha-amylase | *Trichoderma longibrachiatum/ Trichoderma reesei* |
| Porzyme 8100 | Danisco | alpha-amylase | *Bacillus amyloliquefaciens* |
| Porzyme tp100 | Danisco | alpha-amylase | *Bacillus amyloliquefaciens* |
| Ronozyme A | DSM/ Novozymes | alpha-amylase | *Bacillus amyloliquefaciens* |
| Ronozyme AX | DSM | alpha-amylase | *Bacillus amyloliquefaciens* |
| Ronozyme ® RumiStar (L/CT) | DSM/ Novozymes | alpha-amylase | *Bacillus stearothermophilus* expressed in *Bacillus licheniformis* |

In one embodiment, the amylase may be a maltogenic α-amylase from *Bacillus* (see EP 120 693). This amylase is commercially available under the trade name Novamyl™ (Novo Nordisk A S, Denmark). Novamyl is described in detail in International Patent Publication WO 91/104669.

In one embodiment, the amylase is selected from the group consisting of: an α-amylase, a G4-forming amylase, a β-amylase, and a γ-amylase.

In one embodiment, the amylase is derived from an organism selected from the group consisting of: *Bacillus licheniformis, Bacillus amyloliquefaciens, Trichodermna* spp. and *Aspergillus* spp.

It will be understood that one amylase unit (AU) is the amount of enzyme that releases 1 mmol of glucosidic linkages from a water insoluble cross-linked starch polymer substrate per min at pH 6.5 and 37° C. (this may be referred to herein as the assay for determining 1 AU).

In one embodiment, disclosure relates to a composition comprising a multi-strain DFM and amylase. In one embodiment, disclosure relates to a composition comprising a multi-strain DFM, xylanase and amylase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 amylase units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 amylase units/g composition.

C. Protease

The term protease as used herein is synonymous with peptidase or proteinase. The protease may be a subtilisin (E.G. 3.4.21.62) or a bacillolysin (E.G. 3.4.24.28) or an alkaline serine protease (E.G. 3.4.21.x) or a keratinase (E.G. 3.4.X.X).

In one embodiment, the protease is a subtilisin. Suitable proteases include those of animal, vegetable or microbial origin. Chemically modified or protein engineered mutants are also suitable. The protease may be a serine protease or a metalloprotease. e.g., an alkaline microbial protease or a trypsin-like protease.

In one embodiment, the disclosure relates to a composition comprising one or more strains disclosed herein and one or more protease.

In one embodiment, the disclosure relates to a composition comprising one or more strains disclosed herein and one or more xylanase and one or more protease.

In one embodiment, the disclosure relates to a composition comprising one or more strains disclosed herein and one or more amylase and one or more protease.

In one embodiment, the disclosure relates to a composition comprising one or more strains disclosed herein, one or more amylase, one or xylanase, and one or more protease.

Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In another embodiment, the protease may be one or more of the proteases in one or more of the commercial products recited in Table 3.

TABLE 3

Representative examples of commercial proteases.

| Commercial product ® | Company | Protease type | Protease source |
|---|---|---|---|
| Avizyme 1100 | Danisco A/S | Subtilisin | *Bacillus subtilis* |
| Avizyme 1202 | Danisco A/S | Subtilisin | *Bacillus subtilis* |
| Avizyme 1302 | Danisco A/S | Subtilisin | *Bacillus subtilis* |
| Avizyme 1500 | Danisco A/S | Subtilisin | *Bacillus subtilis* |
| Avizyme 1505 | Danisco A/S | Subtilisin | *Bacillus subtilis* |
| Kemzyme Plus Dry | Kemin | Bacillolysin | *Bacillus amyloliquefaciens* |
| Kemzyme W dry | Kemin | Bacillolysin | *Bacillus amyloliquefaciens* |
| Natuzyme | Bioproton | Protease | *Trichoderma longibrachiatum/ Trichoderma reesei* |
| Porzyme 8300 | Danisco | Subtilisin | *Bacillus subtilis* |
| Ronozyme ProAct | DSM/Novozymes | Alkaline serine protease | *Nocardiopsis prasina* gene expressed in *Bacillus licheniformis* |
| Versazyme/Cibenza DP100 | Novus | Keratinase | *Bacillus licheniformis* |

In one embodiment, the protease may be a protease from *B. subtilis*.

In yet another embodiment, the protease may be a Nocardiopsis protease available from Novozymes A/S.

In one embodiment, the protease is selected from the group consisting of subtilisin, a bacillolysin, an alkine serine protease, a keratinase, and a Nocardiopsis protease.

It will be understood that one protease unit (PU) is the amount of enzyme that liberates from the substrate (0.6% casein solution) one microgram of phenolic compound (expressed as tyrosine equivalents) in one minute at pH 7.5 (40 mM $Na_2PO_4$/lactic acid buffer) and 40° C. This may be referred to as the assay for determining 1 PU.

In one embodiment, disclosure relates to a composition comprising a multi-strain DFM and a protease. In another embodiment, disclosure relates to a composition comprising a multi-strain DFM and a xylanase and a protease.

In still another embodiment, the disclosure relates to a composition comprising a multi-strain DFM and an amylase and a protease. In yet another embodiment, the disclosure relates to a composition comprising a multi-strain DFM and a xylanase, an amylase and a protease.

In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 protease units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 protease units/g composition.

III. DFMs and Exogenous Enzymes

In one embodiment, the DFM and exogenous enzymes may be formulated as a liquid, a dry powder or a granule. In one embodiment, the DFMs and exogenous enzymes can be formulated as a single mixture. In another embodiment, the DFMs and the exogenous enzymes can be formulated as separate mixtures. In still another embodiment, separate mixtures of DFMs and the exogenous enzymes can be administered at the same time or at different times. In still another embodiment, separate mixtures of DFMs and the exogenous enzymes can be administered simultaneously or sequentially.

In yet another embodiment, a first mixture comprising DFMs can be administered followed by a second mixture comprising exogenous enzymes. In still another embodiment, a first mixture comprising exogenous enzymes can be administered followed by a second mixture comprising DFMs.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

In another embodiment, the DFM and/or the enzyme(s) may be coated, for example encapsulated. Suitably the DFM and enzymes may be formulated within the same coating or encapsulated within the same capsule. Alternatively one or more of the enzymes may be formulated within the same coating or encapsulated within the same capsule while the DFM can be formulated in a separate coating from the enzymes.

In some embodiments, such as where the DFM is capable of producing endospores, the DFM may be provided without any coating. In such circumstances, the DFM endospores may be simply admixed with one or more enzymes. In the latter case, the enzymes may be coated, e.g. encapsulated, for instance one or more or all of the enzymes may be coated, e.g. encapsulated. The enzymes may be encapsulated as mixtures (i.e. comprising one or more, two or more, three or more or all) of enzymes or they may be encapsulated separately, e.g. as single enzymes. In one preferred embodiment, all enzymes may be coated, e.g. encapsulated, together.

In one embodiment the coating protects the enzymes from heat and may be considered a thermoprotectant.

In another embodiment, the DFMs and exogenous feed enzymes may be mixed with feed or administered in the drinking water. In one embodiment, the dosage range for inclusion into water is about $1 \times 10^3$ CFU/animal/day to about $1 \times 10^{10}$ CFU/animal/day, and more preferably about $1 \times 10^7$ CFU/animal/day.

IV. Feed Additive Composition

In one embodiment, the disclosure relates to a feed additive composition comprising one or more DFMs and one or more exogenous feed enzymes. In one embodiment, the feed additive composition can be formulated in any suitable way to ensure that the formulation comprises viable DFMs and active enzymes.

In one embodiment, the feed additive composition may be used in the form of solid or liquid preparations or alternatives thereof. Examples of solid preparations include powders, pastes, boluses, capsules, ovules, pills, pellets, tablets, dusts, and granules which may be wettable, spray-dried or freeze-dried. Examples of liquid preparations include, but are not limited to, aqueous, organic or aqueous-organic solutions, suspensions and emulsions.

In another embodiment, the feed additive composition can be used in a solid form. In one embodiment, the solid form is a pelleted form. In solid form, the feed additive composition may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In one embodiment the feed additive composition is formulated to a dry powder or granules as described in WO2007/044968 (referred to as TPT granules) or WO 1997/016076 or WO 1992/012645 (each of which is incorporated herein by reference).

In one embodiment the feed additive composition may be formulated to a granule fbr feed compositions comprising: an active agent comprising one or more DFM and one or more exogenous feed enzyme and at least one coating. In one embodiment, the active agent of the granule retains activity after processing. In one embodiment, the active agent of the granule retains an activity level after processing selected from the group consisting of: 50-60% activity, 60-70% activity, 70-80% activity, 80-85% activity, 85-90% activity, and 90-95% activity.

In one embodiment, the active agent retains activity after conditions selected from one or more of: (a) a feed pelleting process; (b) a steam-heated feed pretreatment process; (c) storage; (d) storage as an ingredient in an unpelleted mixture; and (e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

In another embodiment, the granule may contain one coating. The coating may comprise a moisture hydrating material that constitutes at least 55% w/w of the granule. In another embodiment, the granule may contain two coatings. The two coatings may be a moisture hydrating coating and a moisture barrier coating.

In some embodiments, the moisture hydrating coating may be from 25% to 60% w/w of the granule and the moisture barrier coating may be from 2% to 15% w/w of the granule. The moisture hydrating coating may be selected from inorganic salts, sucrose, starch, and maltodextrin and the moisture barrier coating may be selected from polymers, gums, whey and starch.

In yet another embodiment, the granule may be produced using a feed pelleting process and the feed pretreatment process may be conducted between 70° C. and 95° C. for up to several minutes, such as between 85° C. and 95° C.

In one embodiment, the granule may have a moisture barrier coating selected from polymers and gums and the moisture hydrating material may be an inorganic salt. The moisture hydrating coating may be between 25% and 45% w/w of the granule and the moisture barrier coating may be between 2% and 20% w/w of the granule.

In another embodiment, the granule may be produced using a steam-heated pelleting process that may be conducted between 85° C. and 95° C. for up to several minutes.

In some embodiments, the DFM (e.g. DFM endospores for example) may be diluted using a diluent, such as starch powder, lime stone or the like.

In one embodiment, the DFM and the enzymes may be in a liquid formulation suitable for consumption preferably such liquid consumption contains one or more of the following: a buffer, salt, sorbitol and/or glycerol.

In another embodiment, the feed additive composition may be formulated by applying, e.g. spraying, the enzyme(s) onto a carrier substrate, such as ground wheat for example.

In one embodiment, the feed additive composition may be formulated as a premix. By way of example only, the premix may comprise one or more feed components, such as one or more minerals and/or one or more vitamins.

In one embodiment, the DFM and exogenous feed enzymes may be formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In another embodiment, the feed additive composition can be delivered as an aqueous suspension and/or an elixir. The feed additive composition may be combined with various sweetening or flavoring agents, coloring matter or dyes, with emulsifying and/or suspending agents and with diluents such as water, propylene glycol and glycerin, and combinations thereof.

V. Feedstuff

In another embodiment, the disclosure relates to a feed additive composition that may be used as a feed or in the preparation of a feed. The feed may be in the form of a solution or as a solid depending on the use and/or the mode of application and/or the mode of administration.

When used as a feed or in the preparation of a feed, such as functional feed, the feed additive composition may be used in conjunction with one or more of the following: a nutritionally acceptable carrier, a nutritionally acceptable diluent, a nutritionally acceptable excipient, a nutritionally acceptable adjuvant, a nutritionally active ingredient.

In one embodiment, the feed additive composition disclosed herein is admixed with a feed component to form a feedstuff. In one embodiment, the feed may be a fodder, or a premix thereof, a compound feed, or a premix thereof. In one embodiment, the feed additive composition disclosed herein may be admixed with a compound feed, a compound feed component or a premix of a compound feed or to a fodder, a fodder component, or a premix of a fodder.

In one embodiment, fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

Compound feeds can be complete feeds that provide all the daily required nutrients, concentrates that provide a part of the ration (protein, energy) or supplements that only provide additional micronutrients, such as minerals and vitamins. The main ingredients used in compound feed are the feed grains, which include com, soybeans, sorghum, oats, and barley.

A premix, as referred to herein, may be a composition composed of micro-ingredients such as vitamins, minerals, chemical preservatives, antibiotics, fermentation products, and other essential ingredients. Premixes are usually compositions suitable for blending into commercial rations.

In one embodiment, a feedstuff as disclosed herein may comprise one or more feed materials selected from the group comprising cereals, such as small grains (e.g., wheat, barley, rye, oats and combinations thereof) and/or large grains such as maize or sorghum; by products from cereals, such as com gluten meal, Distillers Dried Grain Solubles (DDGS), wheat bran, wheat middlings, wheat shorts, rice bran, rice hulls, oat hulls, palm kernel, and citrus pulp; protein obtained from sources such as soya, sunflower, peanut, lupin, peas, fava beans, cotton, canola, fish meal, dried plasma protein, meat and bone meal, potato protein, whey, copra, sesame; oils and fats obtained from vegetable and animal sources; and minerals and vitamins.

In yet another embodiment, a feedstuff may comprise at least one high fiber feed material and/or at least one by-product of the at least one high fiber feed material to provide a high fiber feedstuff. Examples of high fiber feed materials include: wheat, barley, rye, oats, by products from cereals, such as com gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fiber: protein obtained from sources such as sunflower, lupin, fava beans and cotton In still another embodiment, the feed may be one or more of the following: a compound feed and premix, including pellets, nuts or (cattle) cake; a crop or crop residue: com, soybeans, sorghum, oats, barley, com stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

In one embodiment the feed additive composition of disclosed herein is admixed with the product (e.g. feedstuff). Alternatively, the feed additive composition may be included in the emulsion or raw ingredients of a feedstuff.

In another embodiment, the feed additive composition is made available on or to the surface of a product to be affected/treated.

In still another embodiment, the feed additive compositions disclosed herein may be applied, interspersed, coated and/or impregnated to a product (e.g. feedstuff or raw ingredients of a feedstuff) with a controlled amount of DFM and enzymes.

In yet another embodiment, the DFM and enzymes may be used simultaneously (e.g. when they are in admixture together or even when they are delivered by different routes) or sequentially (e.g. they may be delivered by different routes).

In one embodiment, the DFM and enzymes are applied to the feedstuff simultaneously. In yet another embodiment, the DFM and enzymes are admixed prior to being delivered to a feedstuff or to a raw ingredient of a feedstuff.

In one embodiment, the DFMs in the feed additive compositions disclosed herein can be added in suitable concentrations including but not limited to concentrations in the final feed product that offer a daily dose of from about $2 \times 10^3$ CFU to about $2 \times 10^{11}$ CFU, from about $2 \times 10^6$ to about $1 \times 10^{10}$, and from about $3.75 \times 10^7$ CFU to about $1 \times 10^{10}$ CFU.

In another embodiment, the xylanase in the feed additive composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, and greater than 8000 xylanase units/g feed additive composition.

In one embodiment, the amylase in the feed additive composition comprises 10-50, 50-100, 100-150, 150-200, 200-250, 250-300, 300-350, 350-400, 400-450, 450-500, 500-550, 550-600, 600-650, 650-700, 700-750, and greater than 750 amylase units/g composition.

In still another embodiment, the protease in the feed additive composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 protease units/g composition.

In one embodiment, the feed additive composition will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; or up to about 60 minutes. The term thermally stable means that at least about 75% of the enzyme components and/or DFM that were present/active in the feed additive composition before heating to the specified temperature are still present/active after it cools to room temperature. In one embodiment, at least about 80% of the enzyme components and/or DFM that were present and active in the feed additive composition before heating to the specified temperature are still present and active after it cools to room temperature.

It will be understood that the feed additive composition disclosed herein is suitable for addition to any appropriate feed material.

It will be understood by the skilled person that different animals require different feedstuffs, and even the same animal may require different feedstuffs, depending upon the purpose for which the animal is reared.

In one embodiment, the ratio of DFM to xylanase in the feed includes but is not limited to $6.25 \times 10^1$ CFU DFM: 1 XU enzyme to $2.0 \times 10^9$ CFU: 1 XU enzyme or in the range from $1.88 \times 10^4$ CFU DFM: 1XU enzyme to $1 \times 10^7$ CFU: 1 XU enzyme.

In one embodiment, the ratio of DFM to xylanase in the feed includes but is not limited to $6.25 \times 10^1$ CFU DFM: 10 XU enzyme to $2.0 \times 10^9$ CFU: 10 XU enzyme or in the range from $1.88 \times 10^4$ CFU DFM: 10 XU enzyme to $1 \times 10^8$ CFU: 10 XU enzyme.

In one embodiment, the ratio of DFM to xylanase in the feed includes but is not limited to $6.25 \times 10^1$ CFU DFM: 0.1 XU enzyme to $2.0 \times 10^9$ CFU: 0.1 XU enzyme or in the range from $1.88 \times 10^4$ CFU DFM: 0.1 XU enzyme to $1 \times 10^7$ CFU: 0.1 XU enzyme.

In one embodiment, the ratio of the DFM to amylase in the feed includes but is not limited to from $1.0 \times 10^2$ CFU DFM: 1 AU enzyme to $2.0 \times 10^{10}$ CFU: 1 AU enzyme; or in the range from $3.7 \times 10^4$ CFU DFM: 1 AU enzyme to $1 \times 10^{10}$ CFU: 1 All enzyme.

In one embodiment, the ratio of the DFM to amylase in the feed includes but is not limited to from $1.0 \times 10^2$ CFU DFM: 10 AU enzyme to $2.0 \times 10^{10}$ CFU: 10 AU enzyme; or in the range from $3.7 \times 10^4$ CFU DFM: 10 AU enzyme to $1 \times 10^{10}$ CFU: 10 AU enzyme.

In one embodiment, the ratio of the DFM to amylase in the feed includes but is not limited to from $1.0 \times 10^2$ CFU DFM: 0.1 AU enzyme to $2.0 \times 10^{10}$ CFU: 0.1 AU enzyme; or in the range from $3.7 \times 10^4$ CFU DFM: 0.1 AU enzyme to $1 \times 10^{10}$ CFU: 0.1 AU enzyme.

In one embodiment, the ratio of the DFM to protease in the feed includes but is not limited to from $5.0 \times 10^1$ CFU DFM: 1 PU enzyme to $1 \times 10^9$ CFU: 1 PU enzyme; or in the range from $1.25 \times 10^4$ CFU DFM: 1 PU enzyme to $5.0 \times 10^6$ CFU: 1 PU enzyme.

In one embodiment, the ratio of the DFM to protease in the tied includes but is not limited to from $5.0 \times 10^1$ CFU DFM: 10 PU enzyme to $1 \times 10^9$ CFU: 10 PU enzyme; or in the range from $1.25 \times 10^4$ CFU DFM: 10 PU enzyme to $5.0 \times 10^6$ CFU: 10 PU enzyme.

In one embodiment, the ratio of the DFM to protease in the feed includes but is not limited to from $5.0 \times 10^1$ CFU DFM: 0.1 PU enzyme to $1 \times 10^9$ CFU: 0.1 PU enzyme; or in the range from $1.25 \times 10^4$ CFU DFM: 0.1 PU enzyme to $5.0 \times 10^6$ CFU: 0.1 PU enzyme.

In yet another embodiment, the feedstuff comprises the following components: $1.5 \times 10^8$ CFU/g of DFM product containing *Bacillus licheniformis*, *Bacillus amyloliquefaciens*, and *Bacillus subtilis*; from about 1,000 to about 8,000 units xylanase/g; from about 100 to about 800 units amylase/g; and from about 4000 to about 12,000 units protease/g.

In still another embodiment, the feedstuff comprises the following components: $1.5 \times 10^8$ CFU/g of DFM product containing *Bacillus licheniformis*, *Bacillus amyloliquefaciens*, and *Bacillus subtilis*; about 4,000 units xylanase/g; about 400 units amylase/g; and about 8,000 units protease/g.

In one embodiment, the feedstuff comprises the following components: a xylanase with activity units from 500 XU/kg to 6000 XU/kg of feed; an amylase with activity units from 100 AU/kg to 800 AU/kg of feed; a protease with activity unties from 4000 PU/kg to 12,000 PU/kg of feed; and a DFM with at least 75,000 CFU/g to 1,500,000 CFU/g of feed.

VI. Methods of Administering DFMs and Exogenous Feed Enzymes to an Animal

In one embodiment, the disclosure relates to methods of increasing performance metrics of an animal. In another embodiment, the disclosure relates to methods of increasing performance metrics of a bird. In still another embodiment, the disclosure relates to methods of increasing performance metrics of poultry, including but not limited to broilers, chickens and turkeys.

In yet another embodiment, the disclosure relates to a method comprising administering to an animal a composition comprising DFMs and exogenous feed enzymes. In still another embodiment, the disclosure relates to a method comprising administering to an animal an effective amount of a composition comprising DFMs and exogenous feed enzymes to increase performance of the animal. This effective amount can be administered to the animal in one or more doses. In one embodiment, the animal is poultry. In still another embodiment, the animal is a broiler.

In another embodiment, the disclosure relates to a method comprising administering to an animal an effective amount of a composition comprising DFMs and exogenous feed enzymes to increase average daily feed intake.

In another embodiment, the disclosure relates to a method comprising administering to an animal an effective amount of a composition comprising DFMs and exogenous feed enzymes to increase average daily weight gain.

In another embodiment, the disclosure relates to a method comprising administering to an animal an effective amount of a composition comprising DFMs and exogenous feed enzymes to increase total weight gain.

In another embodiment, the disclosure relates to a method comprising administering to an animal an effective amount of a composition comprising DFMs and exogenous feed enzymes to increase feed conversion, which can be measured by either feed:gain or gain:feed.

In another embodiment, the disclosure relates to a method comprising administering to an animal an effective amount of a composition comprising DFMs and exogenous feed enzymes to increase feed efficiency.

In another embodiment, the disclosure relates to a method comprising administering to an animal an effective amount of a composition comprising DFMs and exogenous feed enzymes to decrease mortality.

In another embodiment, the disclosure relates to a method comprising administering to an animal an effective amount of a composition comprising DFMs and exogenous feed enzymes to decrease actual production costs.

In another embodiment, the disclosure relates to a method comprising administering to poultry an effective amount of a composition comprising DFMs and exogenous feed enzymes to decrease the incidence of paw lesions.

In another embodiment, the disclosure relates to a method comprising administering to poultry an effective amount of a composition comprising DFMs and exogenous feed enzymes to increase the economic value of poultry feet.

In one embodiment, the animal is poultry. In still another embodiment, the animal is a broiler.

In yet another embodiment, the exogenous feed enzymes include but are not limited to xylanase, amylase and protease.

In still another embodiment, the DFM is a multi-strain DFM comprising *B. subtilis* 27 (NRRL B-50105) or a strain having all of the identifying characteristics of the *B. subtilis* 27 (NRRL B-50105); *B. subtilis* strain BS2084 Accession No. NRRL B-50013 or a strain having all of the identifying characteristics of the BS2084 (NRRL B-50013); *B. subtilis* strain 3AP4 (PTA-6506) or a strain having all of the identifying characteristics of the 3AP4 ((PTA-6506); *B. licheniformis* 842 (NRRL B-50516) or a strain having all of the identifying characteristics of the *B. licheniformis* 842; and *B. licheniformis* 21 (NRRL B-50134) or a strain having all of the identifying characteristics of the *B. licheniformis* 21 (NRRL B-50134).

In some embodiments, the one or more *Bacillus* strain(s) is (are) added to an animal's feed at a rate of at least $1 \times 10^4$ CFU/animal/day. For poultry, the one or more *Bacillus* strain(s) is(are) fed at about $1 \times 10^5$ CFU/g feed to about $1 \times 10^{10}$ CFU/g feed. In at least some embodiments, the one or more *Bacillus* strain(s) is fed at about $1 \times 10^5$ CFU/bird/day. Poultry can be fed about $1 \times 10^8$ CFU/bird/day.

The DFM provided herein can be administered, for example, as the strain-containing culture solution, the strain-containing supernatant, or the bacterial product of a culture solution.

Administration of a composition comprising a DFM and exogenous feed enzymes provided herein to an animal can increase the performance of the animal. In one embodiment, administration of a DFM provided herein to an animal can increase the average daily feed intake (ADFI), average daily gain (ADG), or feed efficiency (gain:feed; G:F) (collectively, "performance metrics"). One or more than one of these performance metrics may be improved.

The composition comprising DFMs and exogenous feed enzymes may be administered to the animal in one of many ways. For example, the composition can be administered in a solid form as a veterinary pharmaceutical, may be distributed in an excipient, preferably water, and directly fed to the animal, may be physically mixed with feed material in a dry form, or the composition may be formed into a solution and thereafter sprayed onto feed material. The method of administration of the compositions disclosed herein to the animal is considered to be within the skill of the artisan.

When used in combination with a feed material, the feed material for ruminants can be grain or hay or silage or grass, or combinations thereof. Included amongst such feed materials are corn, dried grain, alfalfa, any feed ingredients and food or feed industry by-products as well as bio fuel industry by-products and corn meal and mixtures thereof. For monogastric diets, the feed material can include corn, soybean meal, byproducts like distillers dried grains with solubles (DDGS), and vitamin/mineral supplement. Other feed materials can also be used.

The time of administration is not crucial so long as the reductive effect on the mycotoxin's toxicity is shown. Administration is possible at any time with or without feed. However, the bacterium is preferably administered with or immediately before feed.

Thus, in at least some embodiments, the effective amount of the composition comprising DFMs and exogenous feed enzymes is administered to an animal by supplementing a feed intended for the animal. As used herein, "supplementing," refers to the action of incorporating the effective amount of bacteria provided herein directly into the feed intended for the animal. Thus, the animal, when feeding, ingests the bacteria provided herein.

The strains, compositions, and methods disclosed herein are further described by the following paragraphs:

1. A composition comprising, consisting of, or consisting essentially of B. subtilis 27 (NRRL B-50105) or a strain having all of the identifying characteristics of the B. subtilis 27 (NRRL B-50105); B. subtilis strain BS2084 Accession No. NRRL B-50013 or a strain having all of the identifying characteristics of the BS2084 (NRRL B-50013); B. subtilis strain 3AP4 (PTA-6506) or a strain having all of the identifying characteristics of the 3AP4 ((PTA-6506); B. licheniformis 842 (NRRL B-50516) or a strain having all of the identifying characteristics of the B. licheniformis 842; and B. licheniformis 21 (NRRL B-50134) or a strain having all of the identifying characteristics of the B. licheniformis 21 (NRRL B-50134) and a xylanase, an amylase and a protease.

2. The composition of paragraph 1 comprising B. subtilis 27 (NRRL B-50105); B. subtilis strain BS2084 Accession No. NRRL B-50013 or a strain having all of the identifying characteristics of the BS2084 (NRRL B-50013); B. subtilis strain 3AP4 (PTA-6506) or a strain having all of the identifying characteristics of the 3AP4 ((PTA-6506); B. licheniformis 842 (NRRL B-50516) or a strain having all of the identifying characteristics of the B. licheniformis 842: and B. licheniformis 21 (NRRL, B-50134) or a strain having all of the identifying characteristics of the B. licheniformis 21 (NRRL B-50134).

3. The composition of paragraph 1 comprising B. subtilis 27 (NRRL B-50105); B. subtilis strain BS2084 Accession No. NRRL B-50013); B. subtilis strain 3AP4 (PTA-6506) or a strain having all of the identifying characteristics of the 3AP4 ((PTA-6506); B. licheniformis 842 (NRRL B-50516) or a strain having all of the identifying characteristics of the B. licheniformis 842; and B. licheniformis 21 (NRRL B-50134) or a strain having all of the identifying characteristics of the B. licheniformis 21 (NRRL B-50134).

4. The composition of paragraph 1 comprising B. subtilis 27 (NRRL B-50105): B. subtilis strain BS2084 Accession No. NRRL B-50013); B. subtilis strain 3AP4 (PTA-6506); B. licheniformis 842 (NRRL B-50516) or a strain having all of the identifying characteristics of the B. licheniformis 842; and B. licheniformis 21 (NRRL B-50134) or a strain having all of the identifying characteristics of the B. licheniformis 21 (NRRL B-50134).

5. The composition of paragraph 1 comprising B. subtilis 27 (NRRL B-50105); B. subtilis strain BS2084 Accession No. NRRL B-50013); B. subtilis strain 3AP4 (PTA-6506); B. licheniformis 842 (NRRL B-50516); and B. licheniformis 21 (NRRL B-50134) or a strain having all of the identifying characteristics of the B. licheniformis 21 (NRRL B-50134).

6. The composition of paragraph 1 comprising B. subtilis 27 (NRRL B-50105): B. subtilis strain BS2084 Accession No NRRL B-50013); B. subtilis strain 3AP4 (PTA-6506): B. licheniformis 842 (NRRL B-50516); and B. licheniformis 21 (NRRL B-50134).

7. The composition of any of paragraphs 1-6, wherein the xylanase is an endo-1,4-β-xylanase or a 1,4-β-xylosidase.

8. The composition of any of paragraphs 1-7, wherein the xylanase is from Bacillus, Trichoderma, Thermomyces, Aspergillus, Penicillium, and Humicola.

9. The composition of any of paragraphs 1-8, wherein the amylase is selected from the group consisting of: an α-amylase, a G4-forming amylase, a β-amylase, and a γ-amylase.

10. The composition of any of paragraphs 1-9, wherein the amylase is an α-amylase.

11. The composition of any of paragraphs 1-10, wherein the amylase is derived from the group consisting of: Bacillus licheniformis, Bacillus amyloliquefaciens, Trichoderma spp. and Aspergillus spp.

12. The composition of any of paragraphs 1-11, wherein the protease is selected from the group consisting of: subtilisin, a bacillolysin, an alkine serine protease, a keratinase, and a Nocardiopsis protease.

13. The composition of any of paragraphs 1-12, wherein the protease is a subtilisin.

14. A method for increasing the performance of an animal comprising administering to an animal an effective amount of a composition to increase performance, wherein the composition comprises B. subtilis 27 (NRRL B-50105): B. subtilis strain BS2084 Accession No. NRRL, B-50013); B. subtilis strain 3AP4 (PTA-6506); B. licheniformis 842 (NRRL B-50516); and B. licheniformis 21 (NRRL B-50134), and a xylanase, amylase, and protease.

15. The method of paragraph 14, wherein the increase in performance comprises an increase in a metric selected from the group consisting of: average daily feed intake, average daily weight gain, total weight gain, feed conversion, which includes both feed:gain and gain:feed, and feed efficiency.

16. The method of any of paragraphs 14-15, wherein the increase in performance comprises a decrease in mortality.

17. The method of any of paragraphs 14-16, wherein the increase in performance comprises reduction in production costs.

18. A method comprising administering to an animal an effective amount of a composition to increase average daily feed intake, wherein the composition comprises B. subtilis 27 (NRRL B-50105); B. subtilis strain BS2084 Accession No. NRRL B-50013); B. subtilis strain 3AP4 (PTA-6506); B. licheniformis 842 (NRRL B-50516); and B. licheniformis 21 (NRRL B-50134), and a xylanase, amylase, and protease.

19. A method comprising administering to an animal an effective amount of a composition to increase average daily weight gain, wherein the composition comprises B. subtilis 27 (NRRL B-50105); B. subtilis strain BS2084 Accession No. NRRL B-50013); B. subtilis strain 3AP4 (PTA-6506); B. licheniformis 842 (NRRL B-50516); and B. licheniformis 21 (NRRL B-50134), and a xylanase, amylase, and protease.

20. A method comprising administering to an animal an effective amount of a composition to increase total weight gain, wherein the composition comprises B. subtilis 27 (NRRL B-50105); B. subtilis strain BS2084 Accession No. NRRL B-50013); B. subtilis strain 3AP4 (PTA-6506); B. licheniformis 842 (NRRL B-50516); and B. licheniformis 21 (NRRL B-50134), and a xylanase, amylase, and protease.

21. A method comprising administering to an animal an effective amount of a composition to increase feed conversion, wherein the composition comprises B. subtilis 27 (NRRL B-50105): B. subtilis strain BS2084 Accession No. NRRL B-50013); B. subtilis strain 3AP4 (PTA-6506); B. licheniformis 842 (NRRL B-50516); and B. licheniformis 21 (NRRL B-50134), and a xylanase, amylase, and protease.

22. A method comprising administering to an animal an effective amount of a composition to increase feed efficiency, wherein the composition comprises B. subtilis 27 (NRRL B-50105); B. subtilis strain BS2084 Accession No. NRRL B-50013); B. subtilis strain 3AP4 (PTA-6506); B.

licheniformis 842 (NRRL B-50516); and *B. licheniformis* 21 (NRRL B-50134), and a xylanase, amylase, and protease.

23. The method of any of paragraphs 14-22, wherein the animal is poultry.

24. The method of any of paragraphs 14-23, wherein the animal is a broiler.

25. A method comprising administering to poultry an effective amount of a composition to reduce paw lesions, wherein the composition comprises *B. subtilis* 27 (NRRL B-50105); *B. subtilis* strain BS2084 Accession No. NRRL B-50013); *B. subtilis* strain 3AP4 (PTA-6506); *B. licheniformis* 842 (NRRL, B-50516); and *B. licheniformis* 21 (NRRL. B-50134), and a xylanase, amylase, and protease.

26. The method of any of paragraphs 14-25, wherein the xylanase is an endo-1,4-β-xylanase or a 1,4-β-xylosidase.

27. The method of any of paragraphs 14-26, wherein the xylanase is from *Bacillus, Trichoderma, Thermomyces, Aspergillus, Penicillium*, and *Humicola*.

28. The method of any of paragraphs 14-27, wherein the amylase is selected from the group consisting of: an α-amylase, a G4-forming amylase, a β-amylase, and a γ-amylase.

29. The method of any of paragraphs 14-28, wherein the amylase is an α-amylase.

30. The method of any of paragraphs 14-29, wherein the amylase is derived from the group consisting of: *Bacillus licheniformis, Bacillus amyloliquefaciens, Trichoderma* spp. and *Aspergillus* spp.

31. The method of any of paragraphs 14-30, wherein the protease is selected from the group consisting of: subtilisin, a bacillolysin, an alkine serine protease, a keratinase, and a Nocardiopsis protease.

32. The method of any, of paragraphs 14-31, wherein the protease is a subtilisin.

33. A feedstuff comprising a feed component and a composition of any of paragraphs 1-14.

34. The feedstuff of paragraph 33, wherein the feed component is selected from the group consisting of: compound feed, a compound feed component, a premix of a compound feed, a fodder, a fodder component, and a premix of a fodder.

35. A method of preparing a feedstuff comprising mixing a feed component with the composition of any of paragraphs 1-14.

36. The method of paragraph 35, wherein the feed component is selected from the group consisting of: compound feed, a compound feed component, a premix of a compound feed, a fodder, a fodder component, and a premix of a fodder.

37. A premix comprising the composition of any of paragraphs 1-14 and one or more vitamins.

38. A method of forming a feed additive composition comprising mixing *B. subtilis* 27 (NRRL B-50105); *B. subtilis* strain BS2084 (Accession No. NRRL B-50013); *B. subtilis* strain 3AP4 (PTA-6506); *B. licheniformis* 842 (NRRL B-50516); and *B. licheniformis* 21 (NRRL B-50134) with a xylanase, an amylase and a protease to form a feed additive composition.

39. A method of forming a feed additive composition comprising: (a) growing, in a liquid nutrient broth *B. subtilis* 27 (NRRL B-50105), *B. subtilis* strain BS2084 (Accession No. NRRL B-50013), *B. subtilis* strain 3AP4 (PTA-6506), *B. licheniformis* 842 (NRRL B-50516); and *B. licheniformis* 21 (NRRL B-50134); (b) separating the microorganism from the liquid broth; and (c) adding a xylanse, an amylase, and a protese to form a feed additive composition.

40. The method of paragraph 39, wherein the microorganisms are grown in separate nutrient broth.

41. A method for reducing the incidence of paw lesions comprising administering to poultry an effective amount of a composition to reduce paw lesions, wherein the composition comprises a multi-strain direct-fed microbial of *B. subtilis* 27 (NRRL B-50105); *B. subtilis* strain BS2084 Accession No. NRRL B-50013); *B. subtilis* strain 3AP4 (PTA-6506); *B. licheniformis* 842 (NRRL B-50516); and *B. licheniformis* 21 (NRRL B-50134), and a xylanase, amylase, and protease.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Introduction

The potential benefits of feeding broilers a composition comprising a multi-strain DFM and exogenous feed enzymes were tested. In this example, the DFM is a mixture of *B. subtilis* strain 27 (NRRL B-50105), *B. subtilis* strain 2084 (NRRL B-50013), *B. subtilis* strain 3A-P4 (PTA-6506), *B. licheniformis* strain 842 (NRRL B-50516) and *B. licheniformis* strain 21 (NRRL B-50134). The exogenous feed enzymes are endo-1,4-beta xylanase, alpha-amylase, and subtilisin protease (hereinafter referred to as XAP).

Materials and Methods:

1440 Cobb 500 male broiler chicks were allocated into 32 pens of 30 chicks in each for the following treatments: control and control+0.05% DFM+0.05% XAP. This trial was replicated twice for each time period. Each time replication consisted of 8 replicates per treatment that were blocked using a randomized complete block design. In all, each treatment had 16 replicates. The XAP product contains 4000 units endo-1,4-beta xylanase/g, 400 units alpha amylase/g and 8000 units subtilisin protease/g. The direct-fed microbial consisted of *Bacillus licheniformis*, and *Bacillus subtilis* summed to a guaranteed $1.5 \times 10^8$ cfu/g of DFM product; which when included at a rate of 1 lb/ton in feed result in a concentration of $7.5 \times 10^4$ cfu/g in the diet.

The control diet is shown in Table 4. DFM and XAP additions were made at the expense of corn. Feed was provided as crumbles for the starter phase and as pellets for all other feed phases. All chicks were vaccinated using a commercially available coccidia vaccine at the hatchery. All pens contained built-up litter as per industry practice. Paw scores were measured in the first time replicate (8 replicates/treatment) at 42 and 56 days of age using a 0 to 2 scale where 0 is no lesions and 2 is severe lesions.

The data were analyzed using JMP® software where time and block are considered in the ANOVA model. Orthogonal contrast analysis was used to investigate treatment effects on bird performance.

TABLE 4

| Ingredient, % of the diet | Starter 0-15 days | Grower 16-31 days | Finisher 32-42 days | Withdrawal 43 to 56 days |
|---|---|---|---|---|
| Corn | 54.595 | 58.093 | 62.081 | 62.517 |
| Soybean Meal | 31.908 | 24.144 | 18.840 | 16.308 |
| Corn DDGS[1] | 5.000 | 10.000 | 12.000 | 15.000 |
| Meat meal blend | 3.000 | 3.000 | 2.500 | 2.000 |
| L-Lysine HCl | 0.211 | 0.268 | 0.253 | 0.249 |
| DL-Methionine | 0.315 | 0.262 | 0.214 | 0.186 |
| L-Threonine | 0.077 | 0.066 | 0.062 | 0.056 |
| Limestone | 0.936 | 0.878 | 0.878 | 0.916 |
| Dicalcium Phosphate | 0.184 | 0.000 | 0.171 | 0.170 |
| Salt | 0.255 | 0.195 | 0.256 | 0.229 |
| Vitamin Premix | 0.500 | 0.500 | 0.500 | 0.500 |
| Trace Mineral Premix | 0.100 | 0.100 | 0.100 | 0.100 |
| Poultry Fat | 1.000 | 1.000 | 1.000 | 1.000 |
| Celite | 1.800 | 1.400 | 1.050 | 0.700 |
| Phytase (2500 FTU/g product) | 0.020 | 0.020 | 0.020 | 0.020 |
| Choline Chloride 60% | 0.100 | 0.075 | 0.075 | 0.050 |

[1]DDGS = dried distiller's grains with solubles
[2]Treatment additions were made at the expense of corn.

Results

Live performance shows significantly improved mortality-corrected feed conversion (mFCR) at 15 (Table 5; P=0.02) and 56 days of age (Table 6; P=0.04) coupled with trends at 31 days (Table 5; P=0.21) and 42 days (Table 6; P=0.16) when DFM+XAP is present. Increased weight (P=0.177) was noted at 56 days of age with DFM+XAP (Table 6). Paw score was improved with the use of DFM+XAP (P=0.0001; Table 6).

Carcass data analysis reveals DFM+XAP increased yield of *Pectoralis minor* (also known as tender; P=0.014) and tended to increase breast meat yield (P=0.128; Table 7) at 42 days. At 56 days, breast (P=0.24) and *Pectoralis major* (P=0.18) tended to increase as a percentage of chill carcass weight (Table 8).

TABLE 7

Yield of carcass and key components at 42 days of age

| Treatment | Chill carcass (%) | Breast[1,2] (%) | Major[1,2] (%) | Minor[1,2] (%) | Legs[1] (%) | Wings[1] (%) |
|---|---|---|---|---|---|---|
| Control | 75.01 | 29.01 | 23.73 | 5.29 b | 32.52 | 10.64 |
| Control + DFM + XAP | 75.20 | 29.48 | 24.03 | 5.44 a | 32.49 | 10.63 |
| P Value | 0.490 | 0.128 | 6.281 | 0.014 | 0.905 | 0.910 |

[1]Yield of breast, major, minor, legs and wings are expressed as a percent of chill carcass weight
[2]Breast refers to deboned major + minor as a percent of chill carcass weight. Major refers to Pectoralis major (also known as the filet); Minor refers to Pectoralis minor (also known as the tender).

TABLE 5

Performance to 15 and 31 days of age

| | 1 to 15 days | | 1 to 31 days | |
|---|---|---|---|---|
| Treatment | Weight (kg) | mFCR (kg:kg) | Weight (kg) | mFCR (kg:kg) |
| Control | 0.532 | 1.195 b | 3.014 | 1.579 |
| Control + DFM + XAP | 0.536 | 1.176 a | 3.151 | 1.566 |
| P value | 0.52 | 0.02 | 0.53 | 0.21 |

TABLE 6

Performance at 42 and 56 days of age

| | 1 to 42 days | | | | 1 to 56 days | | | |
|---|---|---|---|---|---|---|---|---|
| Treatment | Weight (kg) | mFCR (kg:kg) | CC[1] (kcal/kg) | Paw Score[2] | Weight (kg) | mFCR (kg:kg) | CC[1] (kcal/kg) | Paw Score[2] |
| Control | 2.556 | 1.838 | 5570 | 0.82 b | 3.014 | 2.212 a | 7226 | 1.04 b |
| Control + DFM + XAP | 2.578 | 1.806 | 5448 | 0.53 a | 3.151 | 2.129 b | 6757 | 0.38 a |
| P value | 0.59 | 0.16 | 0.32 | 0.036 | 0.177 | 0.04 | 0.121 | 0.0001 |

[1]CC = calorie conversion measured as calories consumed/weight gain.
[2]Paw score was measured in the first time replicate (8 replicates/treatment). Data are based on a 0 to 2 scale where 0 = no lesions and 2 = severe lesions.

TABLE 8

Yield of carcass and key components at 56 days of age

| Treatment | Chill Carcass (%) | Breast[1,2] (%) | Major[1,2] (%) | Minor[1,2] (%) | Legs[1] (%) | Wings[1] (%) |
|---|---|---|---|---|---|---|
| Control | 77.67 | 28.71 | 23.22 | 5.49 | 32.25 | 10.35 |
| Control + DFM + XAP | 77.45 | 29.12 | 23.68 | 5.45 | 32.35 | 10.32 |
| P value | 0.435 | 0.244 | 0.180 | 0.53 | 0.750 | 0.764 |

[1]Yield of breast, major, minor, legs and wings are expressed as a percent of chill carcass weight.
[2]Breast refers to deboned major + minor as a percent of chill carcass weight. Major refers to Pectoralis major (also known as the filet); Minor refers to Pectoralis minor (also known as the tender).

Economic return over feed cost analysis reveals that use of DFM+XAP increases value to the end user by 20 cents/bird at 42 days (Table 9) and 24 cents/bird at 56 days (Table 10).

TABLE 9

Economics on broilers raised to 42 days of age.

| Treatment | Total feed Cost[1] ($/bird) | Cut-up Revenue[2] ($/bird) | Return over Feed Cost ($/bird) |
|---|---|---|---|
| Control | 2.07 | 7.88 | 5.81 |
| Control + DFM + XAP | 2.06 | 8.07 | 6.01 |
| Extra value due to DFM + XAP | 0.01 | 0.19 | 0.20 |

[1]Based on FeedStuffs ingredient prices report as of Aug. 27, 2012
[2]Based on Georgia Dock price of carcass components as of Aug. 22, 2012

TABLE 10

Economics on broilers raised to 56 days of age.

| Treatment | Total feed Cost[1] ($/bird) | Cut-up Revenue[2] ($/bird) | Return over Feed Cost ($/bird) |
|---|---|---|---|
| Control | 3.05 | 10.17 | 7.12 |
| Control + DFM + XAP | 3.02 | 10.38 | 7.36 |
| Extra value due to DFM + XAP | 0.03 | 0.21 | 0.24 |

[1]Based on FeedStuffs ingredient prices report as of Aug. 27, 2012
[2]Based on Georgia Dock price of carcass components as of Aug. 22, 2012

These results demonstrate that birds fed DFM+XAP were more feed and calorie efficient than the controls at market age. Increased *Pectoralis minor* yield and an increasing trend on breast meat yield at 42 days (P=0.12) were seen for DFM+XAP. In addition, at 56 days, *Pectoralis major* (P=0.18) and breast yield (P=0.24) tended to increase with a composition of DFM and XAP. Birds fed DFM+XAP showed a significantly lower incidence of foot pad lessions. Overall, the combination of DFM+XAP benefited conversion and paw quality of broilers.

Example 2

Introduction

The potential benefits of feeding broilers a composition comprising a multi-strain DFM and exogenous feed enzymes were tested. In this example, the DFM is a mixture of *B. subtilis* strain 27 (NRRL B-50105), *B. subtilis* strain 2084 (NRRL B-50013), *B. subtilis* strain 3A-P4 (PTA-6506), *B. licheniformis* strain 842 (NRRL B-50516) and *B. licheniformis* strain 21 (NRRL B-50134). The exogenous feed enzymes are endo-1,4-beta xylanase, alpha-amylase, and subtilisin protease (hereinafter referred to as XAP).

Materials and Methods:

Approximately 480 Cobb 500 mixed sex chicks were assigned to 16 floor pens for this trial. The treatments consisted of Control and Control+0.05% DFM+0.05% XAP; each treatment was replicated 8 times. The XAP product contains 4000 units endo-1,4-beta xylanase/g, 400 units alpha amylase/g and 8000 units subtilisin protease/g. The DFM consisted of *Bacillus licheniformis*, and *Bacillus subtilis* summed to a guaranteed level of $1.5 \times 10^8$ cfu/g of DFM product, which when included at a rate of 1 lb/ton in feed result in a concentration of $7.5 \times 10^4$ cfu/g in the diet.

Three feed phases were used in this trial; the diet composition is shown in Table 11. Salinomycin was used at 60 g/ton as a coccidiostat, no other antibiotics were used.

TABLE 11

Ingredient composition of the base diet

| Ingredient, % of the diet | Starter 0-17 days | Grower 18-28 days | Finisher 29-42 days |
|---|---|---|---|
| Corn | 57.55 | 61.68 | 63.08 |
| Soybean Meal, 48% | 31.62 | 22.56 | 15.72 |
| Corn DDGS[1] | 5.01 | 10.00 | 15.00 |
| Meat meal blend | 3.01 | 3.00 | 3.00 |
| Limestone | 0.92 | 0.79 | 0.86 |
| Soy oil | 0.50 | 0.71 | 0.73 |
| Dicalcium Phosphate | 0.46 | 0.20 | — |
| Salt | 0.36 | 0.34 | 0.32 |
| DL-Methionine | 0.23 | 0.195 | 0.13 |
| L-Lysine | 0.12 | 0.23 | 0.26 |
| Choline chloride, 60% | 0.08 | 0.097 | — |
| Trace mineral premix | 0.08 | 0.08 | 0.08 |
| Vitamin premix | 0.07 | 0.05 | 0.05 |
| L-Threonine, 98% | — | 0.05 | 0.037 |
| Phytase, 10000 FTU/g product | 0.006 | 0.006 | 0.006 |
| Total | 100 | 100 | 100 |

[1]DDGS = dried distiller's grains with solubles
[2]Treatment additions were made at the expense of corn.

Inclusions of DFM and XAP were made at the expense of corn. The trial utilized a randomized complete block design so that each treatment was represented in each block. In this trial, built-up litter in each pen was top-dressed with approximately 4 inches of fresh shavings in each pen prior to bird arrival.

The data were analyzed using JMP® software where block and treatment are considered in the ANOVA model. Orthogonal contrast analysis was used to investigate treatment effects on bird performance.

Results:

Addition of DFM+XAP improved mFCR at 15 days (Table 12; P=0.012) and 42 days (Table 13; P=0.005) of age for broilers raised floor pens. Calorie conversion from 1 to 15 days (Table 12; P=0.01) and 1 to 42 days (Table 13; P=0.0005) was improved with the use of DFM+XAP.

TABLE 12

Performance results to 15 days of age.

| Treatment | 1 to 15 days | | |
|---|---|---|---|
| | Gain (kg) | mFCR (kg:kg) | Calorie conversion (kcal/kg) |
| Control | 0.285 | 1.263 b | 3697 b |
| Control + DFM + XAP | 0.298 | 1.234 a | 3612 a |
| P value | 0.350 | 0.012 | 0.01 |

TABLE 13

Performance results to 42 days of age

| Treatment | 1 to 42 days | | |
|---|---|---|---|
| | Gain (kg) | mFCR (kg:kg) | Calorie Conversion (kcal/kg) |
| Control | 2.351 | 1.710 b | 5161 b |
| Control + DFM + XAP | 2.379 | 1.667 a | 5029 a |
| P value | 0.519 | 0.005 | 0.0005 |

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the disclosure as described. Therefore, it is intended that this invention be limited only by the claims and the equivalents thereof. The disclosures of patents, references and publications cited in the application are incorporated by reference in their entirety herein.

What is claimed is:

1. A feed additive composition consisting essentially of a direct fed microbial (DFM) consisting of strains: *Bacillus subtilis* 27 (Accession No. NRRL B-50105); *Bacillus subtilis* BS2084 (Accession No. NRRL B-50013); *Bacillus subtilis* 3AP4 (Accession No. ATCC PTA-6506); *Bacillus licheniformis* 842 (Accession No. NRRL B-50516); and *Bacillus licheniformis* 21 (Accession No. NRRL B-50134) and a xylanase, an amylase and a protease.

2. The composition of claim 1, wherein the xylanase is an endo-1, 4-β-xylanase or a 1,4-β-xylosidase.

3. The composition of claim 1, wherein the xylanase is from an organism selected from the group consisting of: *Bacillus*, *Trichoderma*, *Thermomyces*, *Aspergillus*, *Penicillium*, and *Humicola*.

4. The composition of claim 1, wherein the amylase is selected from the group consisting of: an α-amylase, a G4-forming amylase, a β-amylase, and a γ-amylase.

5. The composition of claim 1, wherein the amylase is an α-amylase.

6. The composition of claim 1, wherein the amylase is derived from an organism selected from the group consisting of: *Bacillus licheniformis*, *Bacillus amyloliquefaciens*, *Trichoderma* spp. and *Aspergillus* spp.

7. The composition of claim 1, wherein the protease is selected from the group consisting of: subtilisin, a bacillolysin, an alkaline serine protease, a keratinase, and a Nocardiopsis protease.

8. The composition of claim 1, wherein the protease is a subtilisin.

9. A final feed product comprising the feed additive composition of claim 1, wherein the concentration of DFM in the final feed product is from $2 \times 10^3$ CFU/ton to $2 \times 10^{11}$ CFU/ton.

10. A method for increasing the performance of an animal comprising: administering to an animal an effective amount of the feed additive composition of claim 1.

11. The method of claim 10, wherein the increase in performance comprises an increase in a metric selected from the group consisting of: average daily feed intake, average daily weight gain, total weight gain, feed conversion, of feed:gain, feed conversion of gain:feed, and feed efficiency.

12. The method of claim 10, wherein the increase in performance comprises a decrease in mortality.

13. The method of claim 10, wherein the increase in performance comprises reduction in production costs.

14. The method of claim 10, wherein the animal is poultry.

15. The method of claim 10, wherein the animal is a broiler.

16. The method of claim 10, wherein the xylanase is an endo-1,4-β-xylanase or a 1,4-β-xylosidase.

17. The method of claim 10, wherein the amylase is selected from the group consisting of: an α-amylase, a G4-forming amylase, a β-amylase, and a γ-amylase.

18. The method of claim 10, wherein the protease is selected from the group consisting of: subtilisin, a bacillolysin, an alkine serine protease, a keratinase, and a Nocardiopsis protease.

19. A method for reducing the incidence of paw lesions comprising administering to poultry an effective amount of the feed additive composition of claim 1.

20. The method of claim 19, wherein the xylanase is an endo-1,4-β-xylanase or a 1,4-β-xylosidase.

21. The method of claim 19, wherein the protease is selected from the group consisting of: subtilisin, a bacillolysin, an alkine serine protease, a keratinase, and a Nocardiopsis protease.

* * * * *

SEQUENCE LISTING

<160> NUMBER OF SEQ ID NOS: 10

<210> SEQ ID NO 1
<211> LENGTH: 10
<212> TYPE: DNA
<213> ORGANISM: Artificial Sequence
<220> FEATURE:
<223> OTHER INFORMATION: Synthesized

<400> SEQUENCE: 1
ggtgcgggaa                                                          10

<210> SEQ ID NO 2
<211> LENGTH: 10
<212> TYPE: DNA
<213> ORGANISM: Artificial Sequence
<220> FEATURE:
<223> OTHER INFORMATION: Synthesized

<400> SEQUENCE: 2
gtttcgctcc                                                          10

<210> SEQ ID NO 3
<211> LENGTH: 10
<212> TYPE: DNA
<213> ORGANISM: Artificial Sequence
<220> FEATURE:
<223> OTHER INFORMATION: Synthesized

<400> SEQUENCE: 3
gtagacccgt                                                          10

<210> SEQ ID NO 4
<211> LENGTH: 10
<212> TYPE: DNA
<213> ORGANISM: Artificial Sequence
<220> FEATURE:
<223> OTHER INFORMATION: Synthesized

<400> SEQUENCE: 4
aagagcccgt                                                          10

-continued

<210> SEQ ID NO 5
<211> LENGTH: 10
<212> TYPE: DNA
<213> ORGANISM: Artificial Sequence
<220> FEATURE:
<223> OTHER INFORMATION: Synthesized

<400> SEQUENCE: 5
aacgcgcaac                                                          10

<210> SEQ ID NO 6
<211> LENGTH: 10
<212> TYPE: DNA
<213> ORGANISM: Artificial Sequence
<220> FEATURE:
<223> OTHER INFORMATION: Synthesized

<400> SEQUENCE: 6
cccgtcagca                                                          10

<210> SEQ ID NO 7
<211> LENGTH: 483
<212> TYPE: PRT
<213> ORGANISM: Bacillus licheniformis

<400> SEQUENCE: 7

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

```
Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
        290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 8
<211> LENGTH: 1452
<212> TYPE: DNA
<213> ORGANISM: Bacillus licheniformis

<400> SEQUENCE: 8
gcaaatctta atgggacgct gatgcagtat tttgaatggt acatgcccaa tgacggccaa      60
cattggaagc gtttgcaaaa cgactcggca tatttggctg aacacggtat tactgccgtc     120
tggattcccc cggcatataa gggaacgagc caagcggatg tgggctacgg tgcttacgac     180
ctttatgatt tagggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttca ggagaacacc taattaaagc ctggacacat     420
tttcattttc cggggcgcgg cagcacatac agcgatttta atggcattg gtaccatttt     480 gacggaaccg attgggacga gtcccgaaag ctgaaccgca tctataagtt tcaaggaaag     540
gcttgggatt gggaagtttc caatgaaaac ggcaactatg attatttgat gtatgccgac     600
atcgattatg accatcctga tgtcgcagca gaaattaaga gatggggcac ttggtatgcc     660
aatgaactgc aattggacgg tttccgtctt gatgctgtca aacacattaa attttcttt      720 ttgcgggatt gggttaatca tgtcagggaa aaaacgggga aggaaatgtt tacggtagct     780
```

-continued

```
gaatattggc agaatgactt gggcgcgctg gaaaactatt tgaacaaaac aaattttaat    840
cattcagtgt ttgacgtgcc gcttcattat cagttccatg ctgcatcgac acagggaggc    900
ggctatgata tgaggaaatt gctgaacggt acggtcgttt ccaagcatcc gttgaaatcg    960
gttacatttg tcgataacca tgatacacag ccggggcaat cgcttgagtc gactgtccaa   1020
acatggttta agccgcttgc ttacgctttt attctcacaa gggaatctgg ataccctcag   1080
gttttctacg gggatatgta cgggacgaaa ggagactccc agcgcgaaat tcctgccttg   1140
aaacacaaaa ttgaaccgat cttaaaagcg agaaaacagt atgcgtacgg agcacagcat   1200
gattatttcg accaccatga cattgtcggc tggacaaggg aaggcgacag ctcggttgca   1260
aattcaggtt tggcggcatt aataacagac ggacccggtg gggcaaagcg aatgtatgtc   1320
ggccggcaaa acgccggtga gacatggcat gacattaccg gaaaccgttc ggagccggtt   1380
gtcatcaatt cggaaggctg gggagagttt cacgtaaacg gcgggtcggt ttcaatttat   1440
gttcaaagat ga                                                       1452
```

<210> SEQ ID NO 9
<211> LENGTH: 463
<212> TYPE: PRT
<213> ORGANISM: Trichoderma reesei

<400> SEQUENCE: 9

```
Met Lys Leu Arg Tyr Ala Leu Pro Leu Leu Gln Leu Ser Leu Pro
 1               5                  10                  15
Val Leu Ser Ala Asp Thr Ala Ala Trp Arg Ser Arg Thr Ile Tyr Phe
                20                  25                  30
Ala Leu Thr Asp Arg Ile Ala Arg Gly Ser Gly Asp Thr Gly Gly Ser
            35                  40                  45
Ala Cys Gly Asn Leu Gly Asp Tyr Cys Gly Gly Thr Phe Gln Gly Leu
        50                  55                  60
Glu Ser Lys Leu Asp Tyr Ile Lys Gly Met Gly Phe Asp Ala Ile Trp
65                  70                  75                  80
Ile Thr Pro Val Val Thr Ser Asp Asp Gly Gly Tyr His Gly Tyr Trp
                85                  90                  95
Ala Glu Asp Ile Asp Ser Ile Asn Ser His Tyr Gly Ser Ala Asp Asp
            100                 105                 110
Leu Lys Ser Leu Val Asn Ala Ala His Ser Lys Gly Phe Tyr Met Met
        115                 120                 125
Val Asp Val Val Ala Asn His Met Gly Tyr Ala Asn Ile Ser Asp Asp
130                 135                 140
Ser Pro Ser Pro Leu Asn Gln Ala Ser Ser Tyr His Pro Glu Cys Asp
145                 150                 155                 160
Ile Asp Tyr Asn Asn Gln Thr Ser Val Glu Asn Cys Trp Ile Ser Gly
                165                 170                 175
Leu Pro Asp Leu Asn Thr Gln Ser Ser Thr Ile Arg Ser Leu Tyr Gln
            180                 185                 190
Asp Trp Val Ser Asn Leu Val Ser Thr Tyr Gly Phe Asp Gly Val Arg
        195                 200                 205
Ile Asp Thr Val Lys His Val Glu Gln Asp Tyr Trp Pro Gly Phe Val
    210                 215                 220
Asn Ala Thr Gly Val Tyr Cys Ile Gly Glu Val Phe Asp Gly Asp Pro
225                 230                 235                 240
Asn Tyr Leu Leu Pro Tyr Ala Ser Leu Met Pro Gly Leu Leu Asn Tyr
                245                 250                 255
```

Ala Ile Tyr Tyr Pro Met Thr Arg Phe Phe Leu Gln Gln Gly Ser Ser
            260                 265                 270

Gln Asp Met Val Asn Met His Asp Gln Ile Gly Ser Met Phe Pro Asp
        275                 280                 285

Pro Thr Ala Leu Gly Thr Phe Val Asp Asn His Asp Asn Pro Arg Phe
    290                 295                 300

Leu Ser Ile Lys Asn Asp Thr Ala Leu Leu Lys Asn Ala Leu Thr Tyr
305                 310                 315                 320

Thr Ile Leu Ser Arg Gly Ile Pro Ile Val Tyr Tyr Gly Thr Glu Gln
                325                 330                 335

Ala Phe Ser Gly Gly Asn Asp Pro Ala Asn Arg Glu Asp Leu Trp Arg
            340                 345                 350

Ser Gly Phe Asn Ala Gln Ser Asp Met Tyr Asp Ala Ile Ser Lys Leu
        355                 360                 365

Thr Tyr Ala Lys His Ala Val Gly Gly Leu Ala Asp Asn Asp His Lys
    370                 375                 380

His Leu Tyr Val Ala Asp Thr Ala Tyr Ala Phe Ser Arg Ala Gly Gly
385                 390                 395                 400

Asn Met Val Ala Leu Thr Thr Asn Ser Gly Ser Gly Ser Ser Ala Gln
                405                 410                 415

His Cys Phe Gly Thr Gln Val Pro Asn Gly Arg Trp Gln Asn Val Phe
            420                 425                 430

Asp Glu Gly Asn Gly Pro Thr Tyr Ser Ala Asp Gly Asn Gly Gln Leu
        435                 440                 445

Cys Leu Asn Val Ser Asn Gly Gln Pro Ile Val Leu Leu Ser Ser
    450                 455                 460

<210> SEQ ID NO 10
<211> LENGTH: 1392
<212> TYPE: DNA
<213> ORGANISM: Trichoderma reesei

<400> SEQUENCE: 10
atgaagctcc ggtacgctct cccgctgctc ttgcagctct ctttgccggt cctctccgca      60
gacaccgccg cctggaggtc ccgcaccatc tactttgccc tgacagaccg catcgctcgt     120
ggaagcggtg acacgggggg cagtgcgtgt gggaacctgg gggactactg cggtggcacg     180
ttccagggct tggagagcaa gttggactac atcaagggca tgggattcga tgccatctgg     240
atcacacctg ttgtgacgag tgatgatggg ggctaccatg gctattgggc ggaggacatc     300
gactccatca actctcatta tggctctgcg gacgatctca agagtctcgt caacgccgcg     360
catagcaagg gcttctatat gatggtggac gtcgtggcca accacatggg ctacgccaat     420
atctctgacg atagtccctc tccactgaac caggcctcgt cgtatcaccc cgagtgtgat     480
atcgactaca caaccaaac cagcgtcgag aactgctgga tcagcggcct cccggatctc     540
aacacgcaga gctcaaccat ccgcagcctc taccaggact gggtctccaa cctcgtgtcc     600
acgtacggct cgacggcgt ccgcatcgac accgtcaagc acgtcgagca agactactgg     660
cccggcttcg tcaacgccac cggcgtctac tgcatcggcg aggtctttga cggagaccca     720
aactacctgc tgccctacgc cagcctcatg ccgggcctgc tcaactacgc catctactac     780
cccatgacgc gcttcttcct ccagcagggc tcctcgcagg acatggtcaa catgcacgac     840
cagatcggca gcatgttccc cgaccccacc gcgctcggca ccttggtcga acaccacgac     900
aacccgcgct cctgagcat caagaacgac acggccctgc tcaagaacgc gctgacgtac     960

```
accatcctct cgcgcggcat ccccatcgtc tactacggca ccgagcaggc cttctcgggc    1020
ggcaacgacc cggccaacag ggaggacctc tggcgcagcg gcttcaacgc ccagtccgac    1080
atgtacgacg ccatctccaa gctcacctac gccaagcacg ccgtcggcgg cctcgccgac    1140
aacgaccaca agcacctgta cgtcgccgac acggcctacg ccttcagccg cgccggcggc    1200
aacatggtgg ccctgaccac caacagcggc agcgggagct cggcccagca ctgcttcggc    1260
acgcaggtgc ccaacggccg ctggcagaat gtctttgacg agggcaatgg gccgacgtat    1320
tccgccgacg gcaacggcca gctttgcttg aatgtgtcca acggtcagcc cattgtcttg    1380
ctgtcttcgt ga                                                        1392
```